US012781269B2

(12) United States Patent
Jameson et al.

(10) Patent No.: US 12,781,269 B2

(45) Date of Patent: Nov. 3, 2026

(54) DNA AMPLIFICATION BUFFER REPLENISHMENT DURING ROLLING CIRCLE AMPLIFICATION

(71) Applicant: ILLUMINA CAMBRIDGE LIMITED, Cambridge (GB)

(72) Inventors: Nathan Jameson, San Diego, CA (US); Kurt Patterson, San Diego, CA (US); Fabian Block, San Diego, CA (US); Brittany Rohrman, San Diego, CA (US)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 777 days.

(21) Appl. No.: 17/740,072

(22) Filed: May 9, 2022

(65) Prior Publication Data

US 2022/0356515 A1 Nov. 10, 2022

Related U.S. Application Data

(60) Provisional application No. 63/186,675, filed on May 10, 2021.

(51) Int. Cl.
*C12Q 1/6848* (2018.01)
*C12Q 1/6853* (2018.01)

(52) U.S. Cl.
CPC ......... *C12Q 1/6848* (2013.01); *C12Q 1/6853* (2013.01)

(58) Field of Classification Search
CPC .. C12Q 1/6848; C12Q 1/6853; C12Q 1/6844; C12Q 1/68; C12Q 1/6874; C12Q 1/6869; C12Q 1/682; C12Q 2535/122; C12Q 2537/149; C12Q 2565/537; C12Q 2531/125
See application file for complete search history.

(56) References Cited

U.S. PATENT DOCUMENTS

| | | | | |
|---|---|---|---|---|
| 7,057,026 | B2 | 6/2006 | Barnes et al. | |
| 7,211,414 | B2 | 5/2007 | Hardin et al. | |
| 7,315,019 | B2 | 1/2008 | Turner et al. | |
| 7,329,492 | B2 | 2/2008 | Hardin et al. | |
| 7,329,860 | B2 | 2/2008 | Feng et al. | |
| 7,405,281 | B2 | 7/2008 | Xu et al. | |
| 8,039,817 | B2 | 10/2011 | Feng et al. | |
| 8,241,573 | B2 | 8/2012 | Banerjee et al. | |
| 10,077,470 | B2 * | 9/2018 | Vijayan | C12Q 1/6869 |
| 10,246,744 | B2 | 4/2019 | Vijayan et al. | |
| 10,443,098 | B2 | 10/2019 | Vijayan et al. | |
| 10,501,782 | B1 * | 12/2019 | Porter | C12Q 1/6844 |
| 10,584,379 | B2 | 3/2020 | Vijayan et al. | |
| 10,597,643 | B2 | 3/2020 | Iyidogan et al. | |
| 2008/0108082 | A1 | 5/2008 | Rank et al. | |
| 2009/0018024 | A1 | 1/2009 | Church et al. | |
| 2009/0272914 | A1 | 11/2009 | Feng et al. | |
| 2010/0111768 | A1 | 5/2010 | Banerjee et al. | |
| 2012/0270305 | A1 | 10/2012 | Reed et al. | |
| 2013/0178369 | A1 | 7/2013 | Burns et al. | |
| 2013/0217023 | A1 * | 8/2013 | Godwin | C12Q 1/6874 435/6.12 |
| 2016/0017414 | A1 | 1/2016 | Drmanac et al. | |
| 2016/0237488 | A1 | 8/2016 | Ke et al. | |
| 2018/0044727 | A1 | 2/2018 | Vijayan et al. | |
| 2018/0187252 | A1 | 7/2018 | Hunter et al. | |
| 2018/0280975 | A1 | 10/2018 | Kilcoin et al. | |
| 2020/0087637 | A1 | 3/2020 | Iyidogan | |

FOREIGN PATENT DOCUMENTS

| | | |
|---|---|---|
| WO | WO1991/006678 | 5/1991 |
| WO | WO2004/018497 | 3/2004 |
| WO | WO2005/065814 | 7/2005 |
| WO | WO2007/123744 | 11/2007 |
| WO | WO2016/034849 | 3/2016 |

OTHER PUBLICATIONS

Ahern, Holly. Jul. 24, 1995. The Scientist. pp. 20-22 (Year: 1995).*
Cao H, Zhou X, Zeng Y. Microfluidic Exponential Rolling Circle Amplification for Sensitive microRNA Detection Directly from Biological Samples. Sens Actuators B Chem. Jan. 15, 2019;279:447-457. doi: 10.1016/j.snb.2018.09.121. Epub Oct. 4, 2018. PMID: 30533973; PMCID: PMC6284813. (Year: 2019).*
Liu et al. Rolling Circle DNA Synthesis: Small Circular Oligonucleotides as Efficient Templates for DNA Polymerases. Journal of the American Chemical Society 1996 118 (7), 1587-1594. DOI: 10.1021/ja952786k (Year: 1996).*

(Continued)

*Primary Examiner* — Stephen T Kapushoc
*Assistant Examiner* — Kailey Elizabeth Cash
(74) *Attorney, Agent, or Firm* — Mueting Raasch Group

(57) ABSTRACT

Provided include methods, compositions, kits, and systems for replenishing a rolling circle amplification (RCA) reaction in a vessel. The RCA reaction can be initiated by contacting a nucleic acid template and a primer with a loading buffer comprising a DNA polymerase and polymerase extension agents including a divalent metal cation and a polyelectrolyte, followed by replenishing with an amplification buffer to continue the nucleic acid amplification through primer extension. The amplification buffer is different in composition from the loading buffer and does not comprise any DNA polymerase.

18 Claims, 8 Drawing Sheets

(56) References Cited

OTHER PUBLICATIONS

Cao, Xueyan et al. Enhanced specificity and efficiency of polymerase chain reactions using poly(amidoamine) dendrimers and derivatives. The Analyst vol. 134,1 (2009): 87-92. doi: 10.1039/b812176a (Year: 2009).*
Bentley et al., "Accurate whole human genome sequencing using reversible terminator chemistry," Nature 2008, 456(7218), 53-59.
International Search Report and Written Opinion dated Aug. 23, 2022 in PCT Patent Application No. PCT/US2022/028367.
Thermo Scientific, "phi29 DNA Polymerase (10 U/μL)," ThermoFisher Scientific 2023, in 7 pages.
Fréchet and Tomalia, "Dendrimers and Other Dendritic Polymers", John Wiley & Sons, Ltd, 2001.

* cited by examiner

DNA AMPLIFICATION BUFFER REPLENISHMENT DURING ROLLING CIRCLE AMPLIFICATION

RELATED APPLICATIONS

This application claims the benefit under 35 U.S.C. § 119(e) of U.S. Provisional Patent Application Serial No. 63/186,675, filed on May 10, 2021, the content of this related application is incorporated herein by reference in its entirety for all purposes.

BACKGROUND

Field

The present application generally relates to molecular biology and more specifically to amplification and sequencing of nucleic acids.

Description of the Related Art

Rolling circle amplification (RCA) is an efficient method to amplify a circular template nucleic acid to produce long single stranded linear nucleic acid molecules that comprise concatenated copies of the template nucleic acid sequence composition. RCA has been used in many applications, such as nucleic acid sequencing.

SUMMARY

Disclosed herein includes a method of rolling circle amplification (RCA) for nucleic acids. The method comprises, in some embodiments, (a) contacting a circular DNA template and a capture primer with a RCA mixture in a vessel for a first duration to form amplified concatemers of the DNA template, wherein the RCA mixture comprises a DNA polymerase, a dNTP mix, a loading buffer comprising a divalent metal cation and a branched polyelectrolyte species, and (b) introducing an amplification buffer into the vessel after the first duration to form amplified concatemers of the DNA template, wherein the amplification buffer does not comprise any DNA polymerase and comprises the divalent metal cation and the branched polyelectrolyte species.

The vessel can be, for example, a flow cell. The DNA template can be, for example, a single-stranded DNA. In some embodiments, the divalent metal cation is a magnesium cation. In some embodiments, the branched polyelectrolyte species is a dendrimer species, for example poly (amidoamine) (PAMAM) dendrimer. The PAMAM dendrimer can be, for example, a G1 PAMAM, G2 PAMAM, G3 PAMAM, G4 PAMAM, G5 PAMAM, or a combination thereof. In some embodiments, the branched polyelectrolyte species is a polycation .

In some embodiments, the circular DNA template is contacted with the first RCA mixture for about 10 minutes to about 60 minutes before the amplification buffer is introduced into the vessel. In some embodiments, the first duration is about 10 minutes to about 60 minutes, for example about 30 minutes.

The formation of amplified concatemers of the DNA template in step (b) can be faster than the formation of amplified concatemers of the DNA template in step (a), for example the formation of amplified concatemers of the DNA template in step (b) can be at least about 25% faster than the formation of amplified concatemers of the DNA template in step (a).

In some embodiments, the method further comprises sequentially introducing one or more additional amplification buffers to the vessel at least once after step (b), wherein the additional amplification buffers do not comprise any DNA polymerase and comprises the divalent metal cation and the branched polyelectrolyte species. In some embodiments, the method sequentially introduces the additional amplification buffers to the vessel twice, three times, or more after step (b). In some embodiments, at least one of the one or more additional amplification buffers, or both, do not comprise any enzyme.

In some embodiments, the introduction of the first of the additional amplification buffers to the vessel is separated from the introduction of the amplification buffer in step (b) by about 10 minutes to about 60 minutes, for example by about 30 minutes. In some embodiments, the introduction of the each of the additional amplification buffers to the vessel is separated from the introduction of the immediately prior additional amplification buffer by about 10 minutes to about 60 minutes, for example by about 30 minutes. In some embodiments, each introduction of the additional amplification buffers to the vessel is separated from each other by about 10 minutes to about 60 minutes, for example by about 30 minutes.

The amplification buffer can be different in composition from at least one of the additional amplification buffers. In some embodiments, each of the additional amplification buffers is different in composition from any other additional amplification buffer. In some embodiments, one or more of the amplification buffer and the additional amplification buffers has the same composition as the loading buffer except that the amplification buffer and the additional amplification buffers do not comprise the DNA polymerase. In some embodiments, one or more of the amplification buffer and the additional amplification buffers has a higher concentration of the divalent metal cation, a higher concentration of the branched polyelectrolyte species, or both, as compared to the loading buffer.

In some embodiments, the method is performed at about 37° C. The capture primer ca be immobilized on a surface of the vessel. In some embodiments, the loading buffer, the amplification buffer, and/or the additional amplification buffers, comprise DTT, glycerol, one or more surfactants, or a combination thereof. In some embodiments, the divalent metal cation in the amplification buffer is in a concentration of at least 10 mM. The divalent metal cation in the amplification buffer can be, for example, in a concentration at least about 1-fold, 2-fold, 3-fold, 4-fold, 5-fold, 6-fold, 7-fold, 8-fold, 9-fold, or 10-fold higher than in the loading buffer. In some embodiments, the divalent metal cation in the loading buffer is in a concentration from about 0.001 mM to about 10 mM. In some embodiments, the branched polyelectrolyte in the amplification buffer is in a concentration of at least 5 μM. The branched polyelectrolyte in the amplification buffer can be, for example, in a concentration at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 110-fold, 120-fold, 130-fold, 140-fold, or 150-fold higher than in the loading buffer. In some embodiments, the branched polyelectrolyte in the loading buffer is in a concentration from about 0.001 μM to about 1 μM.

In some embodiments, contacting the circular DNA template and the capture primer with the RCA mixture comprises formation of polymerase-nucleic acid complexes, and after introducing the amplification buffer into the vessel, at least about 50% of the DNA polymerase bound to the polymerase-nucleic acid complexes are retained. In some embodiments, after introducing the amplification buffer into the vessel, at least 90% of the polymerases bound to polymerase-nucleic acid complexes are retained. In some embodiments, contacting the circular DNA template and the capture primer with the RCA mixture comprises formation of polymerase-nucleic acid complexes, and after introducing the amplification buffer into the vessel, at most 5% of the DNA polymerase dissociate from the polymerase-nucleic acid complexes. In some embodiments, introducing the amplification buffer into the vessel removes DNA polymerase that is not in the polymerase-nucleic acid complexes from the vessel. The polymerase can be, for example, Phi29 polymerase. In some embodiments, the amplification buffer comprises dNTPs.

Also disclosed herein includes a kit for rolling circle amplification. In some embodiments, the kit comprises a first buffer comprising a divalent metal cation, a branched polyelectrolyte species, and a DNA polymerase, and a second buffer that does not comprise any DNA polymerase and comprises the divalent metal cation and the branched polyelectrolyte species.

The divalent metal cation can be a magnesium cation. In some embodiments, the branched polyelectrolyte species is a dendrimer species. The divalent metal cation in the second buffer can be, for example, in a concentration at least 1-fold, 2-fold, 3-fold, 4-fold, 5-fold, 6-fold, 7-fold, 8-fold, 9-fold, or 10-fold greater than in the first buffer. The branched polyelectrolyte in the second buffer can be, for example, in a concentration at least 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 110-fold, 120-fold, 130-fold, 140-fold, or 150-fold greater than in the first buffer.

In some embodiments, the kit further comprises one or more additional buffers that each does not comprise any DNA polymerase and comprises the divalent metal cation and the branched polyelectrolyte species at concentrations different from the second buffer and each other additional buffers.

BRIEF DESCRIPTION OF THE DRAWINGS

FIGS. 6 and 7 demonstrate the continued activity of the single polymerase amplification of each spot subsequent to addition of replenishment buffer.

DETAILED DESCRIPTION

Figure 1A:
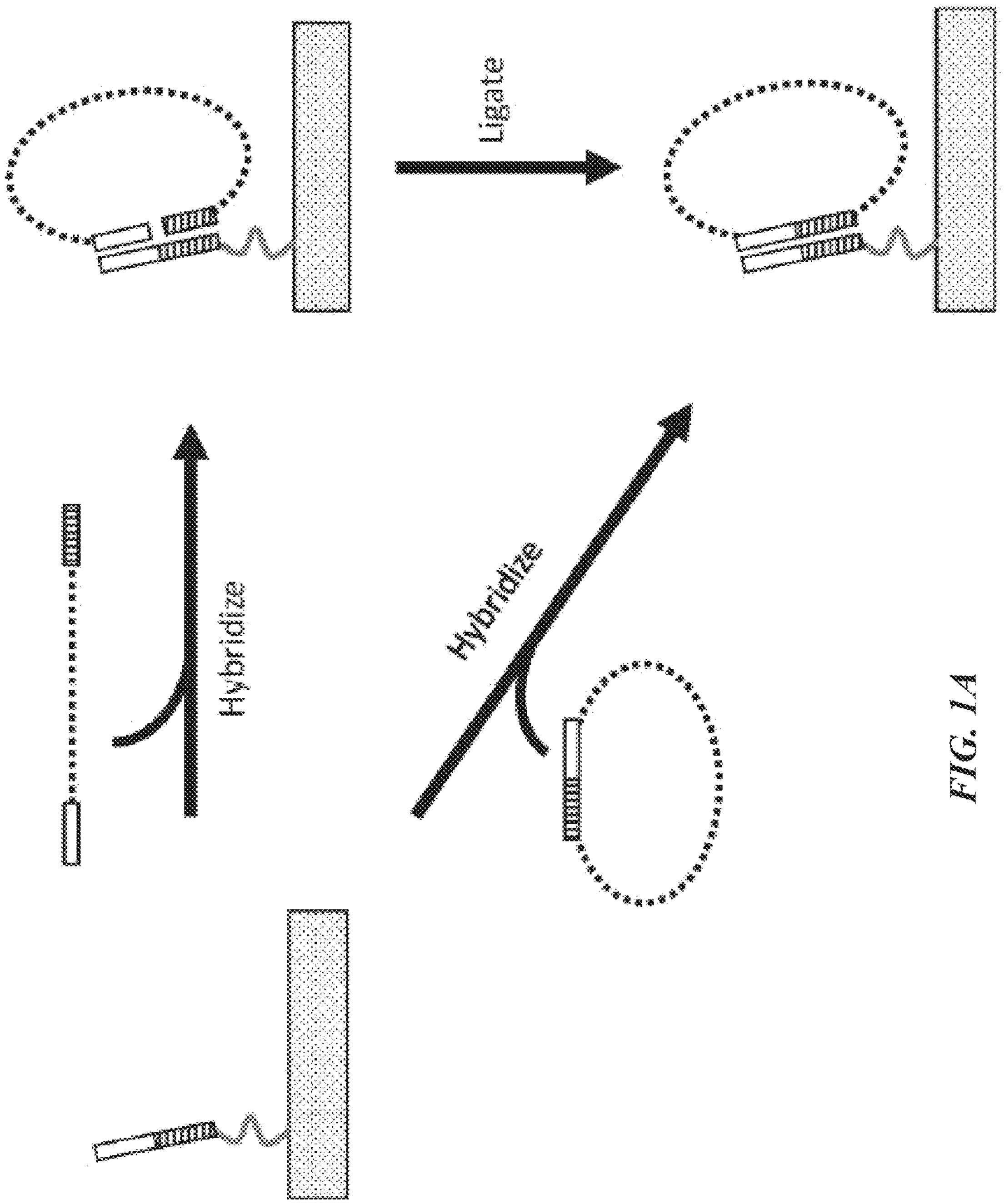
FIG. 1A shows a non-limiting schematic illustration of producing a circular template nucleic acid hybridized to an immobilized nucleic acid primer (e.g. a capture primer).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

DEFINITIONS

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989). For purposes of the present disclosure, the following terms are defined below.

As used herein, the term "immobilized," when used in reference to a molecule, refers to direct or indirect, covalent or non-covalent attachment of the molecule to a surface such as a surface of a solid support. In some configurations, covalent attachment may be preferred, but generally all that is required is that the molecules (e.g. nucleic acids) remain immobilized or attached to the surface under the conditions in which surface retention is intended.

As used herein, the term "nucleotide" refers to a native nucleotide or analog thereof. Examples of nucleotide include, but are not limited to, nucleotide triphosphates (NTPs) such as ribonucleotide triphosphates (rNTPs), deoxyribonucleotide triphosphates (dNTPs), non-natural analogs thereof such as dideoxyribonucleotide triphosphates (ddNTPs), and reversibly terminated nucleotide triphosphates (rtNTPs).

As used herein, the term "primer" refers to a nucleic acid having a sequence that binds to a nucleic acid at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g., a hairpin primer). In some embodiments, the primer can be a first nucleic acid molecule that binds to a second nucleic acid molecule having the template sequence. A primer can consist of, or comprise, DNA, RNA or analogs thereof. A primer can, for example, have an extendible 3' end or a 3' end that is blocked from primer extension.

As used herein, the term "primed-template nucleic acid" refers to a nucleic acid having a double stranded region such that one of the strands functions as a primer and the other strand functions as a template.

As used herein, the term "polymerase-nucleic acid complex" refers to an intermolecular association between a polymerase (e.g., a DNA polymerase) and a nucleic acid (e.g., a template nucleic acid). The polymerase-nucleic acid complex can also comprise, for example, a nucleotide (e.g., a nucleotide that interacts with the template nucleic acid via Watson-Crick hydrogen bonding). In some embodiments, the polymerase-nucleic acid complex that comprises a polymerase, a nucleic acid and a nucleotide is also referred to as a ternary complex.

As used herein, the term "polymerase" refers to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' oxygen moiety of the first strand of the double stranded nucleic acid molecule via a phosphodiester bond, thereby covalently incorporating the nucleotide to the first strand of the double stranded nucleic acid molecule. In some embodiments, a polymerase need not be capable of nucleotide incorporation under one or more conditions used in a method set forth herein. For example, a mutant polymerase may be capable of forming a ternary complex but incapable of catalyzing nucleotide incorporation.

As used herein, a "vessel" is a container that functions to isolate one chemical process (e.g., a binding event; an incorporation reaction; etc.) from another, or to provide a space in which a chemical process can take place. Examples of vessels useful in connection with the disclosed technique include, but are not limited to, flow cells, wells of a multi-well plate; microscope slides; tubes (e.g., capillary tubes); droplets, vesicles, test tubes, trays, centrifuge tubes, features in an array, tubing, and channels in a substrate.

As used herein, the term "circular," when used in reference to a nucleic acid strand, means that the strand has no terminus (that is, the strand lacks a 3' end and a 5' end). Accordingly, the 3' oxygen and the 5' phosphate moieties of every nucleotide monomer in a circular strand is covalently attached to an adjacent nucleotide monomer in the strand. A circular DNA strand can serve as a template for producing a concatemeric amplicon via rolling circle amplification (RCA), wherein each sequence unit of the concatemeric amplicon is the reverse complement of the circular nucleic acid strand. A circular nucleic acid can be double stranded or single stranded. One or both strands in a double stranded nucleic acid can lack a 3' end and a 5' end. One strand in a double stranded nucleic acid can have a gap (absence of at least one nucleotide monomer relative to the other strand) or nick (absence of a phosphodiester bond between two nucleotide monomers), so long as the other strand is circular. In some embodiments, the circular nucleic acid is a double-stranded DNA.

As used herein, the term "concatemer," when used in reference to a nucleic acid molecule, refers to a continuous nucleic acid molecule that contains multiple copies of a common sequence linked in series. Similarly, the term "concatemer," when used in reference to a nucleotide sequence, means a continuous nucleotide sequence that contains multiple copies of a common sequence in series. Each copy of the sequence can be referred to as a "sequence unit" of the concatemer. A sequence unit can have a length of at least 10 bases, 50 bases, 100 bases, 250 bases, 500 bases or more. A concatemer can include at least 2, 5, 10, 50, 100 or more sequence units. A sequence unit can include subregions having any of a variety of functions such as a primer binding region, target sequence region, tag region, unique molecular identifier (UMI), or the like.

As used herein, the term "label" refers to a molecule or a moiety thereof, that provides a detectable characteristic. The detectable characteristic can be, for example, an optical signal such as absorbance of radiation, fluorescence emission, luminescence emission, fluorescence lifetime, luminescence lifetime, fluorescence polarization, luminescence polarization or the like; Rayleigh and/or Mie scattering; binding affinity for a ligand or receptor; magnetic properties; electrical properties; charge; mass; and radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, and the like.

Provided herein include methods, compositions, kits and systems for performing rolling circle amplification (RCA) reactions for nucleic acids. Methods, compositions, kits and systems can, for example, enable more efficient RCA reactions. The method can comprise, for example (a) contacting a circular DNA template and a capture primer with a RCA mixture in a vessel for a duration to form amplified concatemers of the DNA template, wherein the RCA mixture comprises a DNA polymerase, a dNTP mix, a loading buffer comprising a divalent metal cation and a branched polyelectrolyte species, and (b) introducing one or more amplification buffers into the vessel after the first duration to form amplified concatemers of the DNA template, wherein the amplification buffers comprises the divalent metal cation and the branched polyelectrolyte species, and do not comprises any DNA polymerase (e.g., the DNA polymerase in the loading buffer), or comprises DNA polymerase at a concentration below that of the loading buffer.

Figure 1B:
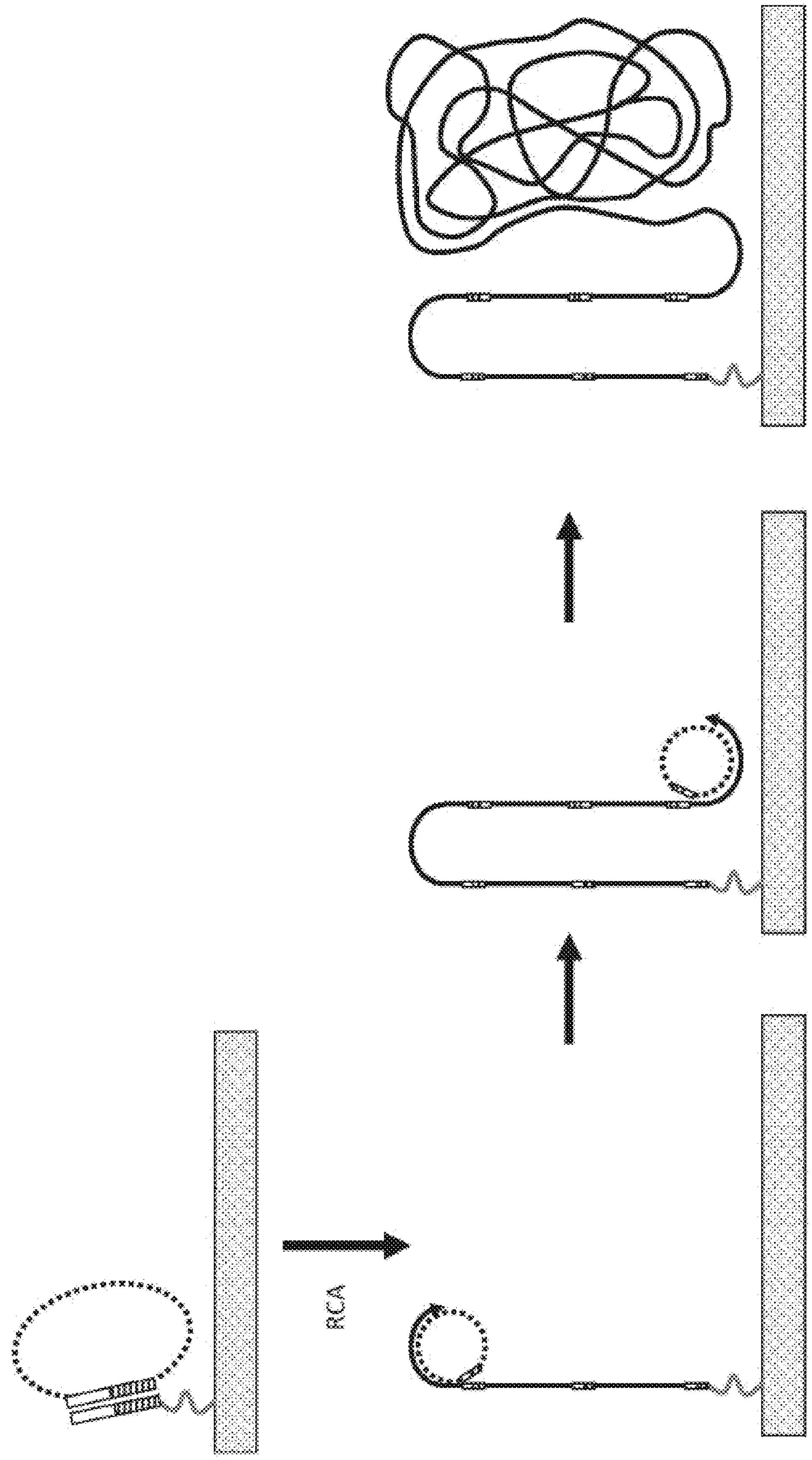
FIG. 1B shows a non-limiting schematic illustration of extending an immobilized capture primer along a circular template nucleic acid via rolling circle amplification to produce amplified concatemers.

Rolling circle amplification (RCA) is a useful method for producing a concatemeric nucleic acid on a solid support (see e.g., FIGS. 1A-B). During RCA, the DNA polymerase depletes reagents required for the amplification of DNA, in particular dNTPs. The processivity and fidelity of the polymerase as well as its ability to form defined clusters is dependent upon dNTP concentration, as well as other factors such as magnesium divalent cation concentration, and may also be influenced by the presence of additional reagents such as PAMAM. The abundance of these factors is limited as the amplification reaction continues due to their relatively limited local availability because of the low volume of reagents which are available within a sequencing flow cell. Simply increasing concentration to overcome this limited abundance is inhibitory due to the antagonistic effect of high initial magnesium or dNTP concentration in a RCA reaction.

Disclosed herein includes a method for replenishing the reagents required for a RCA reaction so that the RCA reaction can continue for long periods of time with minimal loss or reduced loss of polymerase activity and minimal polymerase cost. This replenishment method can, in some embodiments, flush out reagents antagonistic to the enzyme including enzyme seeding inhibitors; PCR inhibitors within the enzyme storage buffer, such as pyrophosphates and excess DTT, glycerol and surfactants; or any combination thereof.

Figure 2:
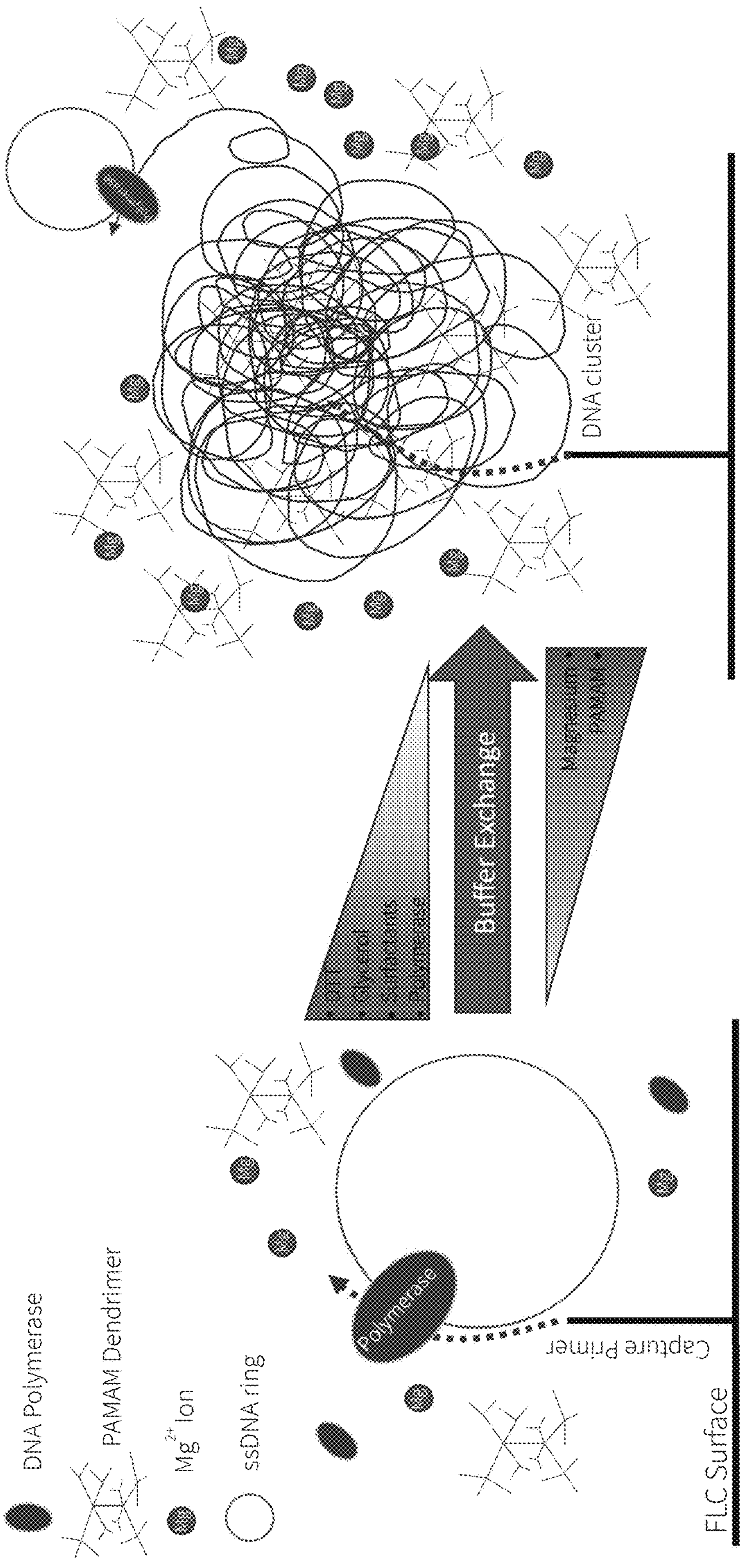
FIG. 2 is a non-limiting schematic illustration of buffer replenishment during rolling circle amplification.

In the method, loading of the polymerase on to the DNA can be carried out in a different reagent mix from the replenishment mix (see e.g., FIG. 2). The original solution (also referred herein to as a loading buffer) can contain a lower concentration of magnesium and PAMAM (as compared to the amplification buffer(s) used for replenishment) to facilitate efficient loading of the enzyme:DNA-ring complex which is attached to a surface of a flow cell (e.g., FIG. 2, left). After an initial incubation in the loading buffer where RCA begins, a flush of amplification buffer (also referred to herein as a replenishment solution) containing higher concentrations of polymerase extension reagents such as magnesium and PAMAM, and without a DNA polymerase or any enzyme is introduced. This replenishment of a modified solution to the flow cell does not remove the DNA polymerase which was already bound to the DNA ring, but can remove excess unbound DNA polymerase. The RCA reaction does not stop during this time, creating a continuous amplification reaction producing a nucleic acid cluster (e.g., DNA cluster shown in FIG. 2, right) with a dynamic and variable secondary structure. The single polymerase per spot can function for a long period of time, for example at least 8 hours. Furthermore, reagent that may be exhausted through activity of an extending polymerase are replenished so as to facilitate ongoing rolling circle extension. In some embodiments, the RCA reaction using only the polymerase loading mix is effective on its own, however the rate of extension of DNA is lower when compared to amplification in the replenishment solution, or the extension rate falls off over time as extension reagents are exhausted. It can be undesirable if treating the replenishment solution as the loading buffer which can significantly reduce the number of enzyme:DNA-ring complexes which are formed. Without being bound by any theory, it is believed that with replenishments the RCA reaction can continue for a much longer time than without replenishment, and given the same amount of time the replenished reaction can produce significantly more amplicons, including copies of the DNA ring. Furthermore, reagents may be added in a replenishment solution at concentrations that are conducive to polymerase extension but that may be inhibitory to polymerase initial binding to a primed template.

The RCA methods described herein can be used to decrease costs of the nucleic acid amplification as compared with the currently available RCA methods. For example, the polymerase is the most expensive component of the reaction mix, so loading the enzyme once at the beginning of the RCA reaction and replenishing with an enzyme-free mix can significantly cut costs in some instances.

The RCA methods disclosed herein can be used in various sequencing platforms, including but not limited to, sequencing-by-synthesis sequencing, sequencing-by-binding sequencing, pH-based sequencing, sequencing by polymerase monitoring, sequencing by hybridization, and other methods of massively parallel sequencing or next-generation sequencing. In some embodiments, the sequencing is carried out as described in U.S. Pat. No. 10,077,470, which is incorporated by reference herein in its entirety. Suitable surfaces for carrying out sequencing include, but are not limited to, a planar substrate, a hydrogel, a nanohole array, a microparticle, or a nanoparticle. In some embodiments, the methods, compositions and systems disclosed herein for performing RCA is used in sequencing-by-synthesis (SBS) methods, compositions and systems.

Divalent Metal Cation

As used herein, the term "divalent metal cation" refers to a catalytic metal cation having a valence of two. The divalent metal cation is required for phosphodiester bond formation between the 3'-OH of a nucleic acid (e.g., a capture primer) and the phosphate of an incoming nucleotide.

The divalent metal cation can be present at different concentrations at different stages of a rolling circle amplification reaction, including but not limited to loading stage and amplification stage. In some embodiments, the divalent metal cation in the loading buffer can be present at a low concentration necessary to facilitate efficient loading of a polymerase (e.g., a DNA polymerase) onto a template nucleic acid to form a polymerase-template nucleic acid complex, thereby initiating the amplification. In some embodiments, the divalent metal cation in an amplification buffer can be present at a higher concentration conducive to primer extension and the nucleic acid amplification as described herein. The concentration of the divalent metal cation can also vary depending on the choice of the divalent metal cation, polymerase, and/or the template nucleic acid. The selection of the divalent metal cation may be based on the polymerase and/or the nucleotides in an amplification reaction. The divalent metal cation can be, for example a magnesium cation ($Mg^{2+}$), manganese cation ($Mn^{2+}$), copper cation ($Cu^{2+}$), cadmium cation ($Cd^{2+}$), and Zinc cation ($Zn^{2+}$). In some embodiments, the divalent metal cation is $Mg^{2+}$. More than one amplification buffer can be used in the methods, compositions and systems described herein. In some embodiments, the type of the divalent metal cation and/or the concentration of the divalent metal cation can be different in some (e.g., two, three, four, five, or six) or all of the amplification buffers.

Branched Polyelectrolyte Species

As used herein, the terms "polyelectrolyte species" or "polyelectrolytes" refer to polymers that, when dissolved in a polar solvent such as water, have a number of charged groups covalently linked to them. Polyelectrolytes can be polyanions, polycations, and polysalts. Branched polyelectrolytes refer to polyelectrolytes having secondary polymer chains linked to a primary backbone, resulting in a variety of polymer architectures such as spherical shaped, H-shaped, pom-pom and comb-shaped polymers.

Branched polyelectrolytes include what are generally referred to as "dendrimers" that are repeatedly branched, roughly spherical three dimensional molecules with nanometer-scale dimensions. Accordingly, the term "dendrimer" used herein refers to repetitively branched molecules having three basic architectural components namely a dendrimer core, repetitive branch cell units and terminal functional groups. A dendrimer core can be a chemical moiety presenting a backbone and at least two anchor atoms, each anchor atom defining a bonding position to a head attachment atom of a branch cell unit. In a dendrimer core, the backbone of the dendrimer core can be any stable chemical moiety having the capability to present anchoring positions for the attachment of branch cell units. In some embodiments, the core backbone structure can be one of aromatic, heteroaromatic rings, aliphatic, or heteroaliphatic rings or chains. In some embodiments, the backbone of the dendrimer core can be one single atom, including but not limited to, C, N, O, S, Si, or P. A "branch cell unit" is a chemical structure presenting one head attachment atom and at least two tail attachment atoms. The head attachment atom defines a bonding position to an anchor atom of a dendrimer core or a tail attachment atom of another branch cell unit. The tail attachment atom defines a bonding position to a head attachment atom of another branch cell unit or to a terminal functional group with the attachment possibly performed directly or indirectly. A generation of branch cell units within a dendrimer defines a shell of the dendrimer as will be understood by a skilled person (see "Dendrimers and other Dendritic polymers" by Jean M. J. Frechet and Donald A. Tomalia 2001). The branch cell units of a generation typically define an interior space inside the dendrimer herein also indicated as interior of shell as will be understood by a skilled person. A "terminal functional group" of a dendrimer is a functional group presented on the outermost part of the dendrimer attached to an end of a branch cell unit. The branch cell units attaching the terminal functional groups typically provide the outer shell or periphery of the dendrimer. Dendrimers can include globular dendrimers, dendrons, hyperbranched polymers, dendrigraft polymers, tecto-dendrimers, core-shell dendrimers, and other types of dendrimers identifiable to a person skilled in the art.

Dendrimers can be classified by a generation number. The common notation for this classification is GX, where X is a number referring to the generation number. For example, a zero generation dendrimer is annotated as G0, a first generation dendrimer is annotated as G1, and so on. The total number of branch cell units (or number of branches) increases exponentially as a function of generation number. In some embodiments, species of dendrimer are available as Generation 0 (G0) up to Generation 10 (G10) with each generation having double the number of branches from the previous generation. For example, G0 PAMAM has 4 branches, G1 PAMAM has 8 branches, and so on. In some embodiments, the dendrimers used herein are G0, G1, G2, G3, G4, or G5 dendrimers, such as G0, G1, G2, G3, G4, or G5 PAMAM.

Dendrimer species can comprise controlled terminal surface chemistry with one or more functional groups that include, but are not limited to, amines, carboxyl, and hydroxyl groups. With different terminal surface groups, dendrimers can be positively charged, negatively charged or neutral.

The dendrimer herein described can be modified by chemical reactions which modify their functional groups so that they have particular binding properties. For example, the high density of nitrogen or oxygen ligands in these dendrimers, along with the possibility of attaching various functional groups to them, make these dendrimers (e.g., PAMAM, PPI, and PEI) attractive as high capacity chelating agents for metal ions such as the metal ions used in RCA amplification reactions.

In some embodiments, the dendrimers used herein comprise positively charged terminal surface groups. For example, a branched polyamine that comprises a protonated structure can interact and form complexes with the negatively charged backbone of DNA. It will be appreciated that adaptor elements may be employed with branched polyamines in the embodiments described herein for alternative purposes or to provide improved binding characteristics for the dendrimer species to the nucleic acid.

Species of dendrimer that can be used in the methods, compositions and systems disclosed herein include, but are not limited to, poly(amidomine) (PAMAM), poly(propylenimine) (PPI), polyethyleneimine (PEI). In some embodiments, the branched polyelectrolyte is PAMAM, for example, a G2 PAMAM dendrimer molecule with 16 branches having the amine ($NH_2$) terminal surface chemistry or G3 PAMAM dendrimer molecule with 32 branches having the amine ($NH_2$) terminal surface chemistry. Non-limiting examples of branched polyelectrolyte also include G4 (64 branches with the amine terminal group) and G5 (128 branches with the amine terminal group) PAMAM dendrimer species.

Similar to the divalent metal cation, the branched polyelectrolyte can be present at different concentrations at different stages of a rolling circle amplification reaction. In some embodiments, the branched polyelectrolyte in the loading buffer can be present at a low concentration necessary to facilitate efficient loading of a polymerase onto a template nucleic acid to form the initial enzyme-template nucleic acid complexes. The branched polyelectrolyte in an amplification buffer can be present at a higher concentration that promotes the formation and stabilization of the nucleic acid clusters formed from primer extension reaction as described in great details below. More than one amplification buffer can be used in the methods, compositions and systems described herein. In some embodiments, the type of the branched polyelectrolyte and/or the concentration of the branched polyelectrolyte can be different in some (e.g., two, three, four, five, or six) or all of the amplification buffers.

Polymerase

Any of a variety of polymerases (e.g., DNA polymerase) can be used in a method or composition set forth herein, for example, to form a polymerase-nucleic acid complex or to carry out primer extensions. Examples of polymerases include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that have the ability to catalyze a polymerization reaction. In some embodiments, the naturally occurring and/or modified variations thereof have the ability to catalyze a polymerization reaction in at least one condition that is not used during formation or examination of a stabilized ternary complex. In some embodiments, the naturally occurring and/or modified variations that participate in polymerase-nucleic acid complexes have modified properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, reduced catalysis rates, catalytic inactivity etc. Mutant polymerases include, for example, polymerases wherein one or more amino acids are replaced with other amino acids, or insertions or deletions of one or more amino acids. Exemplary polymerase mutants that can be used to form a stabilized ternary complex include, for example, those set forth in U.S. Patent Application Publication No. 2020/0087637 A1 published on Mar. 19, 2020, and U.S. Pat. Nos. 10,584,379 and 10,597,643, each of which is incorporated herein by reference. In some embodiments, the polymerase has a strand-displacement activity alone or in combination with a strand displacement factor such as a helicase.

Polymerases used herein can be attached with an exogenous label moiety (e.g. an exogenous fluorophore), which can be used to detect the polymerase. In some embodiments, the label moiety can be attached after the polymerase has been at least partially purified using protein isolation techniques. For example, the exogenous label moiety can be covalently linked to the polymerase using a free sulfhydryl or a free amine moiety of the polymerase. This can involve covalent linkage to the polymerase through the side chain of a cysteine residue, or through the free amino moiety of the N-terminus. An exogenous label moiety can also be attached to a polymerase via protein fusion. Exemplary label moieties that can be attached via protein fusion include green fluorescent protein (GFP), phycobiliproteins (e.g., phycocyanin and phycoerythrin) or wavelength-shifted variants of GFP or phycobiliproteins. In some embodiments, a polymerase is not attached to an exogenous label.

The polymerase can be obtained from various sources. The polymerase can be a DNA polymerase, RNA polymerase, or other types of polymerases such as reverse transcriptase.

Exemplary DNA polymerases include, but are not limited to, bacterial DNA polymerases, eukaryotic DNA polymerases, archaeal DNA polymerases, viral DNA polymerases and phage DNA polymerases. Bacterial DNA polymerases include, but are not limited to, *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include, but are not limited to, DNA polymerases α, β, γ, δ, €, η, ζ, σ, μ, and k, as well as the Revl polymerase (terminal deoxycytidyl transferase) and terminal deoxynucleotidyl transferase (TdT). Viral DNA polymerases include, but are not limited to, T4 DNA polymerase, phi-29 DNA polymerase, GA-1, phi-29-like DNA polymerases, PZA DNA polymerase, phi-15 DNA polymerase, Cp1 DNA polymerase, Cp7 DNA polymerase, T7 DNA polymerase, and T4 polymerase. Additional examples of DNA polymerases include, but are not limited to, thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases can be also be used in the methods, compositions, kits and systems disclosed herein. For example, modified variants of the extremely thermophilic marine archaea *Thermococcus species* 9° N (e.g., Therminator DNA polymerase from New England BioLabs Inc., Ipswich, Mass.) can be used.

Exemplary RNA polymerases include, but are not limited to, viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V; and Archaea RNA polymerase.

Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

Template Nucleic Acids

A template nucleic acid or a nucleic acid template used herein comprises a target sequence and a primer binding region that is complementary to a capture primer used herein such that upon complementary binding between the primer binding region of the template nucleic acid and the capture primer, the capture primer can be extended using the template nucleic acid as a template.

The template nucleic acids used herein can be DNA, including but not limited to genomic DNA, synthetic DNA, amplified DNA, complementary DNA (cDNA) or the like. The template nucleic acids used herein can also be RNA, including but not limited to, mRNA, ribosomal RNA, tRNA or the like. The template nucleic acids can be labeled or non-labeled (e.g., lack exogenous labels).

The template nucleic acids used herein can comprise nucleic acid analogs comprising modifications to the phosphate moiety, the sugar moiety and/or the nitrogenous base of a nucleotide analog. In some embodiments, the nucleic acid analog can include terminators that reversibly prevent subsequent nucleotide incorporation at the 3'-end of the primer. In some embodiments, such as in sequencing-by-binding or sequencing-by-synthesis, a reversible terminator moiety can be modified or removed from a primer, in a process known as "deblocking," allowing for subsequent nucleotide incorporation.

In some embodiments, the template nucleic acids comprise genomic fragments. The template nucleic acid for the RCA reaction disclosed herein can be a single stranded nucleic acid or a double stranded nucleic acid. In some embodiments, the template nucleic acid is a single strand DNA ring.

The template nucleic acid can be a circular nucleic acid template (e.g., a dsDNA or a ssDNA). In some embodiments, the template nucleic acid can be a linear nucleic acid that can be circularized to form a circular nucleic acid template. A variety of methods can be used to prepare a circular template nucleic acid from a linear nucleic acid template for a RCA. For example, the circularization of the linear nucleic acid template can be produced by an enzymatic reaction, for example, by incubation with a ligation enzyme (e.g., a DNA ligase). In some embodiments, the terminal ends of the linear nucleic acid template can be hybridized to a nucleic acid sequence such that the terminal ends come in close proximity (see e.g., FIG. 1A). Incubating with a ligation enzyme can then result in the circularization of the hybridized linear nucleic acid template to generate a circular nucleic acid template. Circular nucleic acid can also be generated by chemical synthesis of suitable linear oligonucleotides followed by circularization of the synthesized oligonucleotide.

The length of a template nucleic acid can be selected to suit a particular application of the methods set forth herein. For example, the length can be about, at least, at least about, at most, at most about 50, 100, 250, 500, 750, 1000, $1\times10^4$, $1\times10^5$ or more nucleotides or base pairs.

The target nucleic acids used herein can be derived from a biological source, a synthetic source or an amplification product. Exemplary organisms from which template nucleic acids can be derived include, for example, a mammal such as a rodent, mouse, rat, rabbit, guinea pig, ungulate, horse, sheep, pig, goat, cow, cat, dog, primate, human or non-human primate; a plant such as *Arabidopsis thaliana,* corn, sorghum, oat, wheat, rice, canola, or soybean; an algae such as *Chlamydomonas reinhardtii;* a nematode such as *Caenorhabditis elegans;* an insect such as *Drosophila melanogaster,* mosquito, fruit fly, honey bee or spider; a fish such as zebrafish; a reptile; an amphibian such as a frog or *Xenopus laevis*; a *dictyostelium discoideum;* a fungi such as *pneumocystis carinii, Takifugu rubripes,* yeast, *Saccharamoyces cerevisiae* or *Schizosaccharomyces pombe;* or a *plasmodium falciparum.* Nucleic acids can be derived from a prokaryote such as a bacterium, *Escherichia coli, staphylococci* or *mycoplasma pneumoniae;* an archaea; a virus such as Hepatitis C virus, influenza virus, coronavirus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual,* 3*rd edition,* Cold Spring Harbor Laboratory, New York (2001) or in Ausubel et al., *Current Protocols in Molecular Biology,* John Wiley and Sons, Baltimore, Md. (1998), each of which is incorporated herein by reference.

Rolling Circle Amplification

Provided herein include methods, kits, systems and compositions for effective rolling circle amplifications of nucleic acids. Generally, a RCA method involves a polymerase extending a primer that is annealed to a circular template such that multiple laps of the polymerase around the circular template produces a concatemeric single stranded nucleic acid that contains multiple tandem repeats, each of the repeats being complementary to the circular template.

FIGS. 1A-B provide a non-limiting schematic illustration of performing a rolling circle amplification for nucleic acids. As shown in FIG. 1A, a nucleic acid primer (indicated by the open and lined rectangles) is attached to a solid support (indicated by the dotted rectangle) via a linker (indicated by the grey line). The primer can be used to capture a target nucleic acid via a primer binding site that is complementary to the primer. In one configuration shown in FIG. 1A, the immobilized primer can hybridize to portions of the primer binding site that are present at opposite ends of a target sequence (the target sequence being indicated by a dotted line and the flanking primer binding site regions being indicated by open and lined rectangles, respectively). The immobilized primer thus functions as a splint that brings together the two ends of the target nucleic acid. The two ends can be ligated while hybridized to a splint nucleic acid to form a circular version of the target nucleic acid. In another configuration shown in FIG. 1A, a target nucleic acid is circularized prior to being hybridized to the immobilized primer on the solid support. Accordingly, the target sequence can be a linear nucleic acid or a circular nucleic acid.

FIG. 1B provides a non-limiting schematic illustration of a single-stranded concatemer being produced via rolling circle amplification of a primed circular template that is hybridized to an immobilized primer. The primer is immobilized in a way that the 3' end is available for polymerase extension (e.g. the primer can be attached at or near its 5' end). The product of the first sub-step is shown as having progressed to a point that two copies of the circular template (two sequence units) have already been produced and the circular template is hybridized to a portion of a third copy (third sequence unit) that is being replicated. Each of the sequence units includes a region that is complementary to the target sequence (indicated by the solid black line) and a region that is complementary to the primer (indicated by the open and lined rectangles). The product of the second sub-step has progressed to the point of having produced nearly six copies of the circular template. FIG. 1B shows the final product of the RCA reaction after the circular template is absent (e.g., has been removed) in the third sub-step. Two regions of the final product are shown for illustrative purposes: a region where the sequence units are delineated (indicative of the concatemeric primary structure of the amplified strand) and a region where the number and conformation of the sequence units is not specified (indicative of the dynamic and variable secondary structure for the cluster as a whole).

An RCA reaction can be terminated by denaturing the polymerase, for example, by heating the sample at 60° C., 65° C., 70° C., 75° C., 80° C., or higher. An RCA reaction can also be terminated by removing one or more components of RCA, such as the polymerase, the dNTPs, or any combination thereof. Components of RCA can be removed by, for example, washing with a washing reagent.

Loading

Disclosed herein includes a method of replenishing reagents for a RCA reaction such that the nucleic acid amplification can occur at an accelerated rate with minimal loss of polymerase activity. The method herein described can comprise a loading step, during which a nucleic acid template (e.g. DNA template) and a capture primer are contacted with a RCA mixture in a vessel for a time duration sufficient to allow loading of a polymerase onto the nucleic acid template to form polymerase-nucleic acid complexes, thereby initiating the RCA amplification. The RCA mixture used in the loading step can comprise a polymerase (e.g., a DNA polymerase), deoxyribonucleoside triphosphates (e.g., a dNTP mix), and a loading buffer comprising a divalent metal cation and a branched polyelectrolyte species.

In some embodiments, the method comprises providing the nucleic acid template, the capture primer and the RCA mixture. The term "providing" as used herein refers to the preparation or delivery of one or more components to a vessel. The template nucleic acid and the capture primer can be provided in any of a variety of ways. In some embodiments, the template nucleic acid and the capture primer can be provided in a solution and then delivered to the vessel by any suitable means. In some embodiments, the capture primer can be attached to a solid support, for example, using covalent or non-covalent attachment chemistries known in the art, prior to being contacted with the template nucleic acid and the RCA mixture (e.g., in FIGS. 1A-B). As used herein, the term "solid support" refers to a rigid substrate that is substantially insoluble in liquids that it contacts. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Any of a variety of liquids, including but not limited to those set forth herein, can be contacted with a solid support.

In some embodiments, a vessel where the template nucleic acid is being contacted with the capture primer and the RCA mixture is a flow cell. As used herein, a "flow cell" is a reaction chamber that includes one or more channels that direct fluid in a predetermined manner to conduct a desired reaction. The flow cell can be coupled to a detector such that a reaction occurring in the reaction chamber can be observed. For example, a flow cell can contain primed template nucleic acid molecules, for example, tethered to a solid support, to which nucleotides and ancillary reagents are iteratively applied and washed away. The flow cell can include a transparent material that permits the sample to be imaged after a desired reaction occurs. For example, a flow cell can include a glass slide containing small fluidic channels, through which polymerases, dNTPs and buffers can be pumped. The glass inside the channels is decorated with one or more primed template nucleic acid molecules to be sequenced. An external imaging system can be positioned to detect the molecules on the surface of the glass. Reagent exchange in a flow cell is accomplished by pumping, drawing, or otherwise "flowing" different liquid reagents through the flow cell. Exemplary flow cells, methods for their manufacture and methods for their use are described in U.S. Pat. App. Publ. Nos. 2010/0111768 A1 published on May 6, 2010 or 2012/0270305 A1 published on Oct. 25, 2012; or WO 05/065814 published on Jul. 21, 2005, each of which is incorporated by reference herein.

Accordingly, in some embodiments, the contacting step can be facilitated by the use of a flow cell. A typical flow cell includes microfluidic valving that permits delivery of liquid reagents (e.g., components of the RCA mixture) through an inlet and removal of liquid reagents from by exiting from an outlet. Flowing liquid reagents through a flow cell can permit reagent mixing and exchange. For example, contacting a nucleic acid template and a capture primer with a RCA mixture can comprise flowing the RCA mixture comprising a polymerase, a dNTP mix, and a loading buffer through a flow cell.

The template nucleic acid, the capture primer, and the RCA mixture can be contacted simultaneously. Alternatively, the template nucleic acid, the capture primer, and the RCA mixture can be contacted sequentially. For example, the template nucleic acid can be contacted with the capture primer to form a primed-template nucleic acid (e.g., in FIG. 1A), which is then contacted with the RCA mixture comprising a polymerase, deoxyribonucleoside triphosphates (dNTPs) or their modified analogues, and a loading buffer. In some embodiments, the template nucleic acid can be contacted with the RCA mixture and then with the capture primer.

The temperature and the length of incubation time for the loading step of a RCA procedure can vary in different embodiments, for example, depending on the polymerase used, the reaction conditions, and the like. In some embodiments, the time duration of contacting a template nucleic acid, a capture primer with a RCA mixture in the loading step can be about 10 minutes to about 60 minutes. For example, the time duration can be, be about, be at most, be at most about, be at least, be at least about, 10, 15, 20, 25, 30, 35, 40, 45, 50, 55, 60 minutes, or a number or a range between any two of these values. In some embodiments, the contacting time duration can be about 30 minutes. The RCA mixture can be incubated with the capture primer and the template nucleic acid at any temperature conducive to the polymerase activity. In some embodiments, contacting a template nucleic acid and a capture primer with a RCA mixture is performed at a substantially isothermal reaction temperature, for example, a temperature that does not vary more than by about 2-3° C. above or below a given temperature. The reaction temperature can be between 20° C. and 70° C., for example 20° C., 25° C., 30° C., 35° C., 40° C., 45° C., 50° C., 55° C., 60° C., 65° C., 70° C., or a number or a range between any two of these values. In some embodiments, the reaction temperature is between 20° C. and 60° C., for example between 20° C. and 50° C. For example, the reaction temperature can be, or be about, 30° C. In some embodiments, the reaction temperature is or is about 37° C.

Contacting a template nucleic acid and a capture primer with a RCA mixture for a time duration under a condition can form amplified concatemers of the template nucleic acid, such as the concatemers shown in FIG. 1B. In some embodiments, contacting a template nucleic acid and a capture primer with a RCA mixture can comprise hybridizing the template nucleic acid and the capture primer (e.g., through the corresponding primer binding region in the template nucleic acid) to form a primed-template nucleic acid and extending the capture primer along the template nucleic acid.

The amplified concatemers of the template nucleic acid can comprise two or more copies of the template nucleic acid. For example, the amplified concatemers formed after the loading step can comprise 2, 3, 4, 5, 6, 7, 8, 9, 10, 11, 12, 13, 14, 15, 16, 17, 20, 21, 22, 23, 24, 25, 26, 27, 28, 29, 30, or more copies of the template nucleic acid. The amplified concatemers of the template nucleic acid can be generated as products of primer extension reactions using the template nucleic acid as a template, such as the RCA reaction illustrated in FIG. 1B.

RCA mixture that is employed in the loading step of a RCA can comprise a polymerase (e.g. a DNA polymerase) and a dNTP mix (including dGTP, dATP, dTTP, dCTP, or any combination thereof). The RCA mixture can contain a loading buffer comprising a divalent metal cation and a branched polyelectrolyte species.

The polymerase can be present at a concentration necessary to facilitate the nucleic acid amplification as will be apparent to a skilled person. In some embodiments, the mole ratio of primers to template nucleic acids can be about $10^{15:1}$ or less. For example, the mole ratio of primers to template nucleic acids can be about $10^{15}$:1, $5\times10^{14}$:1, $10^{14}$:1, $10^{13}$:1, $10^{12}$:1, $10^{11}$:1, $10^{10}$:1, $10^{9}$:1, $10^{8}$:1, $10^{7}$:1, or $10^{6}$:1. In some embodiments, the molar ratio of polymerase to template nucleic acids can be about $1.5\times10^{10}$:1 or less. For example, the molar ratio of polymerase to template nucleic acids can be about 3×$10^9$:1, $10^9$:1, $10^8$:1, $10^7$:1, $10^7$:1, $10^6$:1, $10^6$:1, $10^5$:1, $10^4$:1,$10^3$:1, $10^2$:1, or 50:1.

The dNTPs in the RCA mixture can be in a range of about 10 μM to about 10 mM as will be apparent to a skilled person. In some embodiments, the dNTP concentration is less than 10 mM to avoid hydrogel formation from the amplified concatemers and to remain at a concentration lower than or equal to the amount of divalent metal cation (e.g. magnesium) present in the RCA mixture.

The divalent metal cation in the loading buffer can be present at a concentration necessary to facilitate efficient loading of a polymerase onto a template nucleic acid to form a polymerase-nucleic acid complex, thereby initiating the amplification. In some embodiments, the divalent metal cation is a magnesium cation. In some embodiments, the concentration of a divalent metal cation (e.g. a $Mg^{2+}$) in a loading buffer necessary to allow the initiation of a RCA reaction is from about 0.001 mM to about 10 mM, about 0.1 to 20 mM, or about 1 to 20 mM. For example, the concentration of the divalent metal cation in a loading buffer can be about, at most, or at most about 0.001 mM, 0.05 mM, 0.1 mM, 0.5 mM, 1.0 mM, 1.5 mM, 2 mM, 2.5 mM, 3.0 mM, 3.5 mM, 4.0 mM, 4.5 mM, 5.0 mM, 5.5 mM, 6.0 mM, 6.5 mM, 7.0 mM, 7.5 mM, 8.0 mM, 8.5 mM, 9.0 mM, 9.5 mM, 10 mM, or a number or a range between any two of these values. Optionally, the concentration of the divalent metal cation in a loading buffer can be about 0.01 mM to about 10 mM, from about 0.1 mM to about 10 mM, from about 1 to about 10 mM. Optionally, the concentration of the divalent metal cation in a loading buffer is from 5 to 10 mM.

The branched polyelectrolyte in the loading buffer can be present at a concentration necessary to initiate the RCA amplification. In some embodiments, the branched polyelectrolyte used in the loading buffer comprises PAMAM (e.g. G3 PAMAM). In some embodiments, the concentration of a branched polyelectrolyte in a loading buffer necessary to allow the initiation of a RCA reaction is from about 0.001 μM to about 1 μM. For example, the concentration of the branched polyelectrolyte in a loading buffer can be about, at most, or at most about 0.001 μM, 0.01 μM , 0.02 μM, 0.04 μM, 0.06 μM, 0.08 μM, 0.1 μM, 0.2 μM, 0.3 μM, 04. μM, 0.5 μM, 0.6 μM, 0.7 μM, 0.8 μM, 0.9 μM, 1.0 μM, ora number ora range between any two of these values. Optionally, the concentration of the branched polyelectrolyte in a loading buffer can be about 0.01 μM to about 1.0 μM, about 0.01 μM to about 0.5 μM, or about 0.1 μM.

The low concentration of the divalent metal cation and/or the branched polyelectrolyte in the loading buffer can promote polymerase interacting and binding with the nucleotides and the template nucleic acid to form polymerase-nucleic acid complexes. Therefore, in some embodiments, increasing the concentration of one or both of the divalent metal cation and the branched polyelectrolyte in the loading buffer can inhibit the binding between the polymerase and the primed-template nucleic acids, thus reducing the number of polymerase-nucleic acid template complexes formed (for example, see FIGS. 3-5). For example, increasing the concentration of the divalent metal cation and/or the branched polyelectrolyte in the loading buffer may reduce the number of polymerase-nucleic acid template complexes formed by at least or at least about 10%, 11%, 12%, 13%, 14%, 15%, 16%, 17%, 18%, 19%, 20%, 25%, 30%, 40%, 50%, 75%, 100%, or a number or a range between any two of these values. Accordingly, increasing the concentration of the divalent metal cation and/or the branched polyelectrolyte in the loading buffer may reduce the amplification yield by at least or at least about 10%, 11%, 12%, 13%, 14%, 15%, 16%, 17%, 18%, 19%, 20%, 25%, 30%, 40%, 50%, 75%, 100%, or a number or a range between any two of these values.

The loading buffer can also include other auxiliary reagents necessary for carrying out a RCA reaction such as salts, buffers, small molecules, co-factors, metals and ion as will be apparent to a skilled person. For example, the loading buffer can include Tris, Tricine, HEPES, MOPS, ACES, MES, phosphate-based buffers, and acetate-based buffers. In some embodiments, the loading buffer can include one or more surfactants (e.g. Tween®20 (a polyoxyethylene sorbitol), NP-40), one or more reducing agents (e.g. dithiothreitol), glycerol, or a combination thereof. The loading buffer can include salts such as NaCl, KCl, potassium acetate, ammonium acetate, potassium glutamate, $NH_4Cl$, or $NH_4HSO_4$, which ionize in aqueous solution to yield monovalent cations. The loading buffer can include chelating agents such as EDTA, EGTA, and the like.

Replenishment

The method herein described can comprise a replenishment step following the incubation in the loading buffer, during which an amplification buffer is introduced into the vessel. The amplification buffer can be introduced under conditions that favor the nucleic acid extension reaction. The amplification buffer introduced in the replenishment step is different in composition than the loading buffer introduced in the loading step. In some embodiments, introducing the amplification buffer occurs after the time duration of the loading step. For example, the amplification buffer can be introduced into the vessel 10, 15, 20, 25, 30, 35, 40, 45, 50, 55, 60 minutes after the loading buffer is introduced into the vessel.

The amplification buffer can be introduced into the vessel by pumping, drawing, or otherwise flowing different liquid reagents in the amplification buffer sequentially or simultaneously in a combined or separated solution(s) through the vessel (e.g. flow cell). The amplification buffer can be replenished to the vessel as many times as desired to amplify the template nucleic acids to a sufficient copy number. In some embodiments, one or more additional amplification buffers can be sequentially introduced to the vessel. For example, one or more additional amplification buffers can be introduced to the vessel once, twice, or more times following the introduction of the first amplification buffer. Each introduction of an amplification buffer can be separated from the introduction of an additional amplification buffer by a time period, such as, by about 10 minutes to about 60 minutes, and optionally by about 30 minutes.

Each amplification buffer can be incubated in the vessel with the polymerase-nucleic acid complexes for a desired amount of time (for example, 5 minutes, 10 minutes, 20 minutes, 30 minutes, 45 minutes, 60 minutes, or a number or a range between any two of these values) and at any temperature conducive to enzyme activity. The incubation temperature for the replenishment step can be the same as or different from the incubation temperature used for the loading step. The amplification buffer can be incubated in the vessel at a temperature between about 20° C. and about 60° C. or between about 20° C. and about 50° C. Optionally, the reaction temperature is between about 30° C. and 40° C. (e.g. about 37° C.).

A reagent removal or wash procedure can be performed between any of a variety of steps set forth herein. For example, a washing step can be included following the loading step and prior to a replenishment step. A washing step can also be performed between any two replenishment steps. A washing step can be used to remove one or more of the reagents that are present in a reaction vessel. The one or more reagents to be removed from the vessel in the washing step can include reagents antagonistic to the polymerase activity, including, for example, enzyme seeding inhibitors and PCR inhibitors within the enzyme storage buffer, such as pyrophosphates and excess DTT, glycerol and surfactants. In some embodiments, the reagent to be removed from the vessel in a washing step can be the excess polymerase in solution. The polymerase can be removed from a vessel under conditions that will wash away the excess polymerase in solution without causing removal of the polymerase bound to the template nucleic acid.

Each of the one or more amplification buffers used herein can have a same or different composition with respect to one another. For example, each of the one or more amplification buffers can have a same or different concentration of the divalent metal cation and/or a same or different concentration of the polyelectrolytes.

Delivery of additional polymerase is not necessary in the replenishment step, which provides an advantage in reducing cost and time required to prepare additional polymerase. Therefore, the one or more amplification buffers including the one or more additional amplification buffers do not comprise a polymerase. For example, one or more of the amplification buffer and the additional amplification buffers can have the same composition as the loading buffer except that the amplification buffer and the additional amplification buffers do not comprise the polymerase (e.g. DNA polymerase), thus reducing the total amount of polymerase required for carrying out a RCA reaction. In some embodiments, replenishing with a polymerase in an amplification buffer not only increases the cost but can also reduce the efficiency of amplification. For example, in some embodiments the amplification efficiency can be reduced by about, at least, at least about 20%, 30%, 40%, 50%, 60%, 70%, 80%, 90%, 100%, or a number or a range between any two of these values (for example, see FIG. 4). In some embodiments, the replenishment of the amplification buffer can remove excess polymerase in solution, but does not remove the polymerase already bound to the nucleic acid template (e.g. the DNA ring).

In some embodiments, one or more of the amplification buffer and the additional amplification buffers has a different composition from the loading buffer. For example, one or both of the divalent metal cation and the branched polyelectrolyte in an amplification buffer can be in a higher concentration than in the loading buffer.

The divalent metal cation in the amplification buffer and/or the one or more additional amplification buffers can be present at a concentration in favor of nucleic acid amplification. In some embodiments, the concentration of a divalent metal cation (e.g. a $Mg^{2+}$) in an amplification buffer is from about 10 mM to about 50 mM. For example, the concentration of the divalent metal cation in an amplification buffer can be about, at least, or at least about 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 34 mM, 35 mM, 36 mM, 37 mM, 38 mM, 39 mM, 40 mM, 41 mM, 42 mM, 43 mM, 44 mM, 45 mM, 46 mM, 47 mM, 48 mM, 49 mM, 50 mM, or a number or a range between any two of these values. In some embodiments, the concentration of the divalent metal cation in an amplification buffer is about, at least, or at least about 50, 75, 100, 150, 200, 250, 350, 400, 450, 500, 550, 600, 650, 700, 750, 800, 850, 900, 950, 1000%, or a number or a range between any two of these values, higher than the concentration of the divalent metal cation in a loading buffer. Optionally, the concentration of the divalent metal cation in an amplification buffer is about, at least, or at least about 100, 200, 300, 400 or 500% higher than the concentration of the divalent metal cation in a loading buffer. In some embodiments, the concentration of the divalent metal cation in an amplification buffer is about, at least, or at least about 1-fold, 2-fold, 3-fold, 4-fold, 5-fold, 6-fold, 7-fold, 8-fold, 9-fold, 10-fold, or a number or a range between any two of these values, higher than the concentration of the divalent metal cation in a loading buffer.

The branched polyelectrolyte in the amplification buffer and/or the one or more additional amplification buffers can be present at a concentration that favors the nucleic acid amplification and further stabilizes the formed nucleic acid clusters. In some embodiments, the concentration of a branched polyelectrolyte (e.g., PAMAM) in an amplification buffer is from about 0.5 μM to 20 about 1 μM to 50 or about 2 μM to 100 μM. For example, the concentration of the branched polyelectrolyte in an amplification buffer can be about, at least, or at least about 0.5 μM, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, or a number or a range between any two of these values. In some embodiments, the concentration of the branched polyelectrolyte in an amplification buffer is about, at least, or at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, or a number or a range between any of these values, higher than the concentration of the branched polyelectrolyte in a loading buffer.

The amplification buffer used herein can further include reagents that may be exhausted through activity of an extending polymerase so as to facilitate ongoing rolling circle extension, including, for example, dNTPs.

In some embodiments, the formation of amplified concatemers of the nucleic acid template following the introduction of an amplification buffer in the replenishment step is faster than the formation of amplified concatemers of the nucleic acid template prior to the introduction of the amplification buffer (e.g., in the loading step). In some embodiments, by replenishing a RCA reaction with an amplification buffer comprising the divalent metal cation and the branched polyelectrolyte in a higher concentration than in the loading buffer, the amplification rate of the RCA reaction can be increased by 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any two of these values. As used herein, the term "amplification rate" is the speed at which an amplification reaction such as a RCA reaction takes place and can be defined as proportional to the increase in the concentration of a product per unit time and/or to the decrease in the concentration of a reactant per unit time. In some embodiments, an amplification rate in a RCA reaction can be measured by the number of repeat units (or the copies of the template nucleic acids) in the amplified concatemers produced within a given time period. In some embodiments, by replenishing with an amplification buffer in a RCA reaction, the number of copies of the template nucleic acids produced within a given time period can be increased by 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any two of these values.

In some embodiments, replenishing a RCA reaction with an amplification buffer described herein can remove the excess polymerase in solution with minimal removal of the polymerase already bound to the template nucleic acids. For example, using the methods and compositions disclosed herein, after introducing the amplification buffer into the vessel, about, at least or at least about 50%, 55%, 60%, 65%, 70%, 75%, 80%, 85%, 90%, 95%, 96%, 97%, 98%, 99%, 100%, or a number or a range between any two of these numbers, of the polymerases can be retained in the plurality of polymerase-nucleic acid complexes. In some embodiments, using the methods and compositions disclosed herein, about, at most, or at most about 5%, 10%, 15%, 20%, 25%, 30%, 35%, 40%, 45%, or 50% of the polymerases can dissociate from the plurality of polymerase-nucleic acid complexes. In some embodiments, at most 5%, 10%, or 20% of the polymerases can dissociate from the plurality of polymerase-nucleic acid complexes. In some embodiments, the high concentration of the divalent metal cation and/or the branched polyelectrolyte in the amplification buffer can prevent the dissociation of polymerases from the polymerase-nucleic acid complexes. Accordingly, delivery of more polymerase to the vessel following the loading step is unnecessary when the polymerase is substantially retained in the polymerase-nucleic acid complexes, thus providing a saving of time and resources that would otherwise be spent preparing more polymerase.

Accordingly, in some embodiments, replenishing a RCA reaction with an amplification buffer comprising the divalent metal cation and the branched polyelectrolyte in a higher concentration than in the loading buffer can increase the processivity of a polymerase. The term “processivity”, when used in reference to an amplification reaction, is defined as the ability of a polymerase (e.g. DNA polymerase) to carry out continuous nucleic acid amplification reaction on a template nucleic acid without frequent dissociation. The processivity can be measured by the average number of nucleotides incorporated by a polymerase on a single association/disassociation event. In some embodiments, using the methods and compositions disclosed herein, the processivity of a polymerase in an amplification reaction can be increased by 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any two of these values. In a non-limiting example, using the methods and compositions disclosed herein, the processivity of Phi29 polymerase can increase from about 70 kb (see e.g., the description at thermofisher.com/order/catalog/product/EP0091#/EP0091) to over 2 Mb (e.g., about 2 Mb-6.6 Mb) (see e.g., Example 3).

In some embodiments, the RCA described herein is performed initially in the presence of low concentrations of reagents (e.g., the divalent metal cation and the branched polyelectrolyte), which facilitates the initial formation of the polymerase-nucleic acid complexes. The RCA is then replenished with higher concentrations of the divalent metal cation and the branched polyelectrolyte without any additional polymerase, which can continue the amplification process with an accelerated amplification rate while substantially retaining the polymerases bound to the primed-template nucleic acids (see e.g., FIG. 5). Moreover, with the replenishment of the amplification buffer, the amplification reaction can continue for a prolonged time period with minimal loss of polymerase activity (see e.g., FIGS. 6-7). For example, in some embodiments, a RCA reaction herein described can continue for 1, 2, 3, 4, 5, 6, 7, 8, 9, 10 hours without the need of supplementing with any additional polymerase.

The methods and compositions herein described can achieve higher yield of nucleic acid amplification over a given period of time by at least about 2-fold (e.g., 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any two of these values).

A non-limiting example of methods, compositions and systems for performing RCA for nucleic acids is disclosed herein. For example, a rolling circle amplification (RCA) mix containing a DNA polymerase, dNTP mix, and a loading buffer containing low concentrations of magnesium and PAMAM (e.g., 7 mM magnesium chloride and 0.1 μM G3 PAMAM G3; or 10 mM magnesium chloride and a desirable concentration of PAMAM G3), can be introduced to a vessel (e.g., a flow cell) containing primers (e.g., embedded capture primers in a 3D surface) hybridized to a single stranded DNA (ssDNA) ring. The loading buffer can contain, for example, 1000 U/mL enzyme in an enzyme storage buffer containing 5% glycerol, 5 mM Tris-HCl pH 7.5, 0.01 mM EDTA, 0.1 mM DTT, 10 mM KCl, 0.05% NP-40, 0.05% Tween®20. The RCA mix can be incubated, for example isothermally, at a desired temperature (e.g., 37° C.) for a desired set period of time (for example, 5 minutes, 10 minutes, 20 minutes, 30 minutes, 45 minutes, 60 minutes, or a number or a range between any two of these values) to generate amplification products. During this time period, the DNA polymerase can complex with the ssDNA ring and begin the rolling circle amplification process, copying the DNA of the ring many times over, forming the beginnings of a DNA cluster. After the set incubation time, a new solution (e.g., an amplification buffer with the same base buffer as the loading buffer but containing higher concentration of reagents conducive for extension, such as magnesium and PAMAM (e.g. 30 mM magnesium chloride and 10 μM PAMAM G3) which does not contain enzyme can be introduced into the vessel (or in some cases which contains an enzyme at a lower concentration than an initial reaction) supplementing or replacing the loading buffer. In some embodiments, the new solution can contain 30 mM magnesium chloride, 10 uM PAMAG G3 and no enzyme. The new solution is to be incubated in the vessel for a desired set amount of time (for example, 5 minutes, 10 minutes, 20 minutes, 30 minutes, 45 minutes, 60 minutes, or a number or a range between any two of these values) at a desired temperature (e.g., about 37° C. or other temperature conducive to enzyme activity) to allow further RCA reaction to occur within the vessel. It can be advantageous that DNA amplification occurs in the presence of the new solution at a faster rate than the first incubation in the loading buffer. This new solution (the amplification buffer) can then be replenished to the vessel as many times as desired to amplify DNA to a sufficient copy number. Exemplary advantages of the methods disclosed herein are also shown in Examples 2-3 which demonstrate higher yield of DNA amplification using the replenishment methods disclosed herein.

As disclosed herein, the methods and compositions for replenishment can, for example, processivity of polymerase (e.g., Phi29 polymerase). Without being bound to any particular theory, it is believed that in some instances, high PAMAM can block polymerases from binding and low PAMAM in the initiation buffer can allow the enzyme to bind more easily. Once the polymerase is bound (in the presence of the initiation buffer) and replenishment buffer is provided to replace the initiation buffer, high PAMAM can, in some embodiments, keep the cluster organized, and high salts screens charge to help the DNA stay compact.

Applications in Sequencing

In some embodiments, RCA herein described can produce a linear concatemeric nucleic acid molecule, which takes the form of a random coil, commonly referred to as a "picosphere." A picosphere can be immobilized to a surface suitable for sequencing (e.g., via hybridizing to a universal capture oligonucleotide on the surface of a sequencing substrate). The universal capture oligonucleotide has a sequence that is unrelated to any specific target sequence of interest and thus can be used to capture any target sequences. In some embodiments, the universal capture oligonucleotide can hybridize to the universal priming sequence in the picospheres. In some embodiments, the universal capture oligonucleotide is a barcode sequencing primer. In some embodiments, the picospheres is attached to the surface through ionic interactions, via covalent linkages, or mediated through binding of attached ligands (e.g., biotin and streptavidin). In some embodiments, one or several sequencing primers are hybridized to the picosphere before or after attachment to the surface for sequencing.

Therefore, the methods, compositions and systems disclosed herein for performing a rolling circle amplification can be used in nucleic acid sequencing, for example, in sequencing-by-binding (SBB) or in sequencing-by-synthesis (SBS) methods, compositions and systems.

"Sequencing-by-binding" refers to a sequencing technique wherein specific binding of a polymerase and cognate nucleotide to a primed template nucleic acid is used for identifying the next correct nucleotide to be incorporated into the primer strand of the primed template nucleic acid. The specific binding interaction need not result in chemical incorporation of the nucleotide into the primer. The specific binding interaction can precede chemical incorporation of the nucleotide into the primer strand or precedes chemical incorporation of an analogous, next correct nucleotide into the primer. Thus, identification of the next correct nucleotide can take place without incorporation of the next correct nucleotide.

Sequencing by binding has been described, for example, in U.S. Pat. Nos. 10,443,098 and 10,246,744, and US Pat. App. Pub. No. 2018/0044727 published on Feb. 15, 2018; the content of each is incorporated herein by reference in its entirety. Briefly, in SBB, the polymerase undergoes conformational transitions between open and closed conformations during discrete steps of a reaction. In one step, the polymerase binds to a primed template nucleic acid to form a binary complex, also referred to herein as the pre-insertion conformation. In a subsequent step, an incoming nucleotide is bound and the polymerase fingers close, forming a pre-chemistry conformation comprising the polymerase, a primed template nucleic acid and a nucleotide, wherein the bound nucleotide has not been incorporated. This step, also referred to herein as an examination step, is followed by removal of the nucleotide (can be labeled or unlabeled nucleotide) without incorporation, and is then followed by de-blocking of the extended strand 3' end so as to render it suitable for extension. Unlabeled, 3' blocked nucleotides are then added, followed by a chemical incorporation step wherein a phosphodiester bond is formed with concomitant pyrophosphate cleavage from the nucleotide (nucleotide incorporation), to form an extension strand that has been extended by one base and that is not competent for further extension without modification. Unincorporated blocked extension bases are removed and labeled bases added, so that they can from ternary complexes at positions where they base pair with the template. These ternary complexes are assayed for fluorescence or other output to determine the identity of the paired base, and then the process is repeated through removal of the labeled base, chemical modification of the extending strand to reveal a 3'OH, and contacting with a population of 3' blocked, unlabeled nucleotides for another single base extension.

The examination step can, for example, involve providing a primed template nucleic acid and contacting the primed template nucleic acid with a polymerase (e.g., a DNA polymerase) and one or more test nucleotides being investigated as the possible next correct nucleotide. The polymerase configuration and/or interaction with the primed template nucleic acid and further with a nucleotide can be monitored during an examination step to identify the next correct base in the template nucleic acid. In some embodiments, the SBB procedure includes a monitoring step that monitors or measures the interaction between the polymerase and the primed template nucleic acid in the presence of the test nucleotides. In some embodiments, the examination step determines the identity of the next correct nucleotide without requiring incorporation of that nucleotide (e.g. either without, or before chemical linkage of that nucleotide to the 3'-end of the primer through a covalent bond). For example, the primer of the primed template nucleic acid molecule can include a blocking group that precludes enzymatic incorporation of an incoming nucleotide into the primer. In some embodiments, the reaction mixture used in the examination step comprises catalytic metal ions at a low or deficient level to prevent the chemical incorporation of the nucleotide into the primer of the primed template nucleic acid. In some embodiments, the reaction mixture used in the examination step comprises a stabilizer that stabilize ternary complexes while precluding incorporation of any nucleotide into the primer, such as a non-catalytic metal ion that inhibits polymerization.

Generally, an examination step involves binding a polymerase to the polymerization initiation site of a primed template nucleic acid in a reaction mixture comprising one or more nucleotides, and monitoring the interaction. An examination step can, for example, include one or more of the following substeps: (1) providing a primed template nucleic acid (i.e., a template nucleic acid molecule hybridized with a primer that optionally may be blocked from extension at its 3'-end); (2) contacting the primed template nucleic acid with a reaction mixture that includes a polymerase and at least one nucleotide; (3) monitoring the interaction of the polymerase with the primed template nucleic acid molecule in the presence of the nucleotide(s) and without chemical incorporation of any nucleotide into the primed template nucleic acid; and (4) determining from the monitored interaction the identity of the next base in the template nucleic acid (i.e., the next correct nucleotide). Examination typically involves detecting polymerase interaction with a template nucleic acid. Detection may include optical, electrical, thermal, acoustic, chemical and mechanical means. The examination step of the sequencing reaction can repeat 1, 2, 3, 4 or more times prior to the optional incorporation step.

In SBS, a reaction mixture used in the examination step can include 1, 2, 3, or 4 types of nucleotide molecules. The nucleotides can be selected from dATP, dTTP (or dUTP), dCTP, and dGTP. The examination reaction mixture can comprise one or more triphosphate nucleotides and one or more diphosphate nucleotides. A ternary complex can form between the primed template nucleic acid, the polymerase, and any one of the four nucleotide molecules so that four types of ternary complexes may be formed.

An incorporation step can be concurrent with or separate from the examination step. In some embodiments of an SBB procedure, the examination step is followed by an incorporation step that adds one or more complementary nucleotides to the 3' end of the primer component of the primed template nucleic acid. The polymerase, primed template nucleic acid and newly incorporated nucleotide produce a post-chemistry conformation. Both pre-chemistry conformation and the post-chemistry conformation can be referred to as a ternary complex, each comprising a polymerase, a primed template nucleic acid and a nucleotide, wherein the polymerase is in a closed state and facilitates interaction between a next correct nucleotide and the primed template nucleic acid. During the incorporation step, divalent catalytic metal ions, such as $Mg^{2+}$, mediate a chemical step involving nucleophilic displacement of a pyrophosphate (PPi) by the 3'-hydroxyl of the primer terminus. The polymerase returns to an open state upon the release of PPi.

The incorporation step may be facilitated by an incorporation reaction mixture. The incorporation reaction mixture can have a different composition of nucleotides than the examination reaction. For example, the examination reaction can include one type of nucleotide and the incorporation reaction can include another type of nucleotide. By way of another example, the examination reaction comprises one type of nucleotide and the incorporation reaction comprises four types of nucleotides, or vice versa. The examination reaction mixture can be altered or replaced by the incorporation reaction mixture.

In some embodiments, an examination step is followed by removal of the labeled nucleotide without being incorporated, and is then followed by de-blocking of the 3' end of the primer (or extended primer) of the primed template nucleic acid so as to render it suitable for extension. Unlabeled, 3' blocked nucleotides are then added, followed by a chemical incorporation step wherein a phosphodiester bond is formed with concomitant pyrophosphate cleavage from the nucleotide (nucleotide incorporation), to form an extension strand that has been extended by one base and that is not competent for further extension without modification. Unincorporated blocked extension bases are removed and labeled bases added, so that they can from ternary complexes at positions where they base pair with the template. These ternary complexes are assayed for fluorescence or other output to determine the identity of the paired base, and then the process is repeated through removal of the labeled base, chemical modification of the extending strand to reveal a 3'OH, and contacting with a population of 3' blocked, unlabeled nucleotides for another single base extension.

In some embodiments, the methods, compositions and systems disclosed herein can be used in one or more steps of a SBB procedure that involves nucleotide incorporation. For example, the methods, systems, and compositions herein disclosed can be used in the incorporation step, either following or concurrent with the examination step, of a SBB procedure to allow nucleotide incorporation and primer extension.

In some embodiments, a SBB procedure uses two different reaction mixtures: an examination reaction mixture in the examination step and an incorporation reaction mixture in the incorporation step. The reaction mixtures typically include reagents that are commonly present in polymerase based nucleic acid synthesis reactions. Reaction mixture reagents can include, but are not limited to, enzymes (e.g. polymerase), dNTPs, template nucleic acids, primers, salts, buffers, small molecules, co-factors, metals, and ions.

The incorporation reaction mixture can, for example, comprise one or more nucleotides (e.g., same or different types) and polymerase extension reagents including a divalent metal cation and a branched polyelectrolyte, in which one or both of the divalent metal cation and the branched polyelectrolyte is in a higher concentration as compared to the examination reaction mixture. For example, the concentration of the divalent metal cation in the incorporation reaction mixture is about, at least, or at least about 1-fold, 2-fold, 3-fold, 4-fold, 5-fold, 6-fold, 7-fold, 8-fold, 9-fold, 10-fold, or a number or a range between any two of these values, higher than the concentration of the divalent metal cation in the examination reaction mixture. In some embodiments, the concentration of the branched polyelectrolyte in the incorporation reaction mixture is about, at least, or at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, or a number or a range between any two of these values, higher than the concentration of the branched polyelectrolyte in the examination reaction mixture. In some embodiments, the concentration of a divalent metal cation (e.g., a $Mg^{2+}$) in the incorporation reaction mixture is from about 10 mM to about 50 mM (e.g., 10, 15, 20, 25, 30, 35, 40, 45, 50 mM, or a number or a range between any two of these two values). In some embodiments, the concentration of a branched polyelectrolyte (e.g., a PAMAM) in the incorporation reaction mixture is from about 0.5 μM to 20 μM (e.g. 0.5, 1, 2, 4, 6, 8, 10, 12, 14, 16, 18, 20 μM, or a number or a range between any two of these two values). In some embodiments, the incorporation reaction mixture does not comprise a polymerase.

Accordingly, in some embodiments, the method of sequencing-by-binding can comprise replacing the examination reaction mixture used in the examination step with the incorporation reaction mixture herein described in the incorporation step. In some embodiments, the method of sequencing-by-binding can comprise washing the immobilized primed template nucleic acid molecule to remove one or more components of the examination reaction mixture (e.g. excess polymerase and reagents antagonistic to the polymerase activity) before introducing the incorporation reaction mixture.

The examination and incorporation reaction mixtures used in the methods, systems, and compositions of a SBB procedure can include other molecules or reagents generally present in a nucleic acid polymerization reaction. Description of SBB reaction mixtures and related methods and uses in a SBB procedure can be found, for example, in U.S. Pat. Nos. 10,443,098 and 10,246,744, each of which is incorporated herein by reference.

In some embodiments, the methods, systems, and compositions herein disclosed can be used to produce (or synthesize) one or more strands of a nucleic acid concatemer for sequencing-by-binding. The one or more strands of a nucleic acid concatemer can be produced using a rolling circle amplification method herein described with a loading buffer and an amplification buffer having different compositions. For example, a rolling circle amplification reaction can be initiated with a loading buffer having a divalent metal cation and a branched polyelectrolyte in a low concentration and then replenished with an amplification buffer having the divalent metal cation and the branched polyelectrolyte in a high concentration. Delivery of additional polymerase is not necessary in any of the replenishment steps, which provides an advantage in reducing cost and time required to prepare additional polymerase. The produced concatemers can then be sequenced by hybridizing a sequencing primer to a primer binding site in a sequence unit of a concatemer and extending the primer along the concatemer to determine the sequence. In some embodiments, one or more strands of a nucleic acid concatemer can form a nucleic acid cluster, which can be stabilized through the interaction between the positive charges carried by the branched polyelectrolyte and the negative charges carried by the nucleic acid cluster. The nucleic acid cluster can comprise a plurality of first strand concatemer strand along with a plurality of second strand concatemers that are complementary to the first strand concatemers. The second strand concatemers can be produced, for example, by rolling circle amplification or by multiple displacement amplification performed on the first strand concatemers. Any one of the strands produced can be sequenced. For example, the first strand of concatemer and the one or more second strands of concatemers can be sequenced sequentially or concurrently with different sequencing primers.

The methods, systems, and compositions herein disclosed can also be used in sequencing-by-synthesis (SBS). SBS generally involves the enzymatic extension of a nascent primer through the iterative addition of nucleotides against a template strand to which the primer is hybridized. SBS differs from SBB, above, in that labeled nucleotides are incorporated into the extending strand, assayed and then the label is removed or deactivated, and the 3' block removed, to iteratively sequence a template. In SBB, a labeled base does not need to be incorporated into an extending strand. Rather, ternary complex formation is assayed, usually for the presence of a labeled base but sometimes for the presence of a labeled polymerase or other feature, after which point the complex is disassembled and a 3' blocked, unlabeled base is used to extend the primer strand. Briefly, SBS can be initiated by contacting target nucleic acids, attached to sites in a flow cell, with one or more labeled nucleotides, DNA polymerase, etc. Those sites where a primer is extended using the target nucleic acid as template will incorporate a labeled nucleotide that can be detected. Detection can include scanning using an apparatus or method set forth herein. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the vessel (before or after detection occurs). Washes can be carried out between the various delivery steps. The cycle can be performed n times to extend the primer by n nucleotides, thereby detecting a sequence of length n. Exemplary SBS procedures, reagents and detection components that can be readily adapted for use with a method, system or apparatus of the present disclosure are described, for example, in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Accordingly, a method of sequencing-by-synthesis can comprise introducing into a vessel (e.g. a flow cell) a replenishment mixture comprising one or both of the divalent metal cation and the branched polyelectrolyte at a high concentration herein described (e.g., the concentrations used in an amplification buffer). For example, a method of sequencing-by-synthesis can comprise hybridizing a sequencing primer to a primer binding site in a sequence unit of a concatemer and extending the sequencing primer along the concatemer to determine the sequence of a template nucleic acid of the concatemer. The replenishment mixture can be introduced after the sequencing primer is hybridized to the primer binding site in the sequence unit of the concatemer and before the primer extension takes place. In some embodiments, the replenishment mixture is introduced after the primer extension takes place. In some embodiments, the primer extension can include repeated cycles of adding a reversibly terminated nucleotide to the sequencing primer and deblocking the reversibly terminated nucleotide on the sequencing primer. The replenishment mixture can be delivered to the vessel as many times as desired to accommodate the number of cycles required to sequence the concatemer. Delivery of additional polymerase is not necessary in any of the replenishment steps.

In some embodiments, a SBS procedure is initiated with an initiation mixture comprising one or both of a divalent metal cation and a branched polyelectrolyte at a low concentration herein described (e.g. the concentrations used in a loading buffer), and then replenished with the replenishment mixture comprising one or both of the divalent metal cation and the branched polyelectrolyte at a high concentration herein described (e.g., the concentrations used in an amplification buffer). For example, In some embodiments, the concentration of the divalent metal cation (e.g., a $Mg^{2+}$) of the replenishment mixture used in one or more steps of a SBS procedure can be from about 10 mM to about 50 mM (e.g., 10, 15, 20, 25, 30, 35, 40, 45, 50 mM, or a number or a range between any two of these two values). In some embodiments, the concentration of the branched polyelectrolyte (e.g., a G3 PAMAM) of the replenishment mixture used in one or more steps of a SBS procedure can be from about 0.5 μM to 20 μM (e.g., 0.5, 1, 2, 4, 6, 8, 10, 12, 14, 16, 18, 20 μM, or a number or a range between any two of these values). In some embodiments, the replenishment mixture used in the SBB procedure does not comprise a polymerase. In some embodiments, the method of sequencing-by-synthesis can comprise, after the primer hybridization, replacing or altering the initiation mixture with the replenishment mixture or one or more components of the replenishment mixture to achieve a desired concentration of the one or more components (e.g. the divalent metal cation and/or the branched polyelectrolyte) as described herein.

Similar to SBB described above, the methods, systems, and compositions herein disclosed can also be used to produce (or synthesize) one or more strands of a nucleic acid concatemer for sequencing-by-synthesis.

Systems and Kits

Provided herein also include systems and kits for performing rolling circle amplifications of nucleic acids. Systems disclosed herein can include a vessel, solid support or other apparatus for carrying out a nucleic acid amplification. For example, the system can include an array, flow cell, multi-well plate, test tube, channel in a substrate, collection of droplets or vesicles, tray, centrifuge tube, tubing or other convenient apparatus. The apparatus can be removable, thereby allowing it to be placed into or removed from the system. As such, a system can be configured to process a plurality of apparatus (e.g. vessels or solid supports) sequentially or in parallel. The system can include a fluidic component configured to deliver one or more reagents set forth herein (e.g., polymerase, primer, template nucleic acid, nucleotides, loading buffer, amplification buffer, or mixtures of such components). The fluidic system can be configured to deliver reagents to a vessel or solid support, for example, via channels or droplet transfer apparatus (e.g., electrowetting apparatus). Any of a variety of detection apparatus can be configured to detect the vessel or solid support where reagents interact. Exemplary systems having fluidic and detection components those set forth in US Pat. App. Pub. No. 2018/0280975A1 published on Oct. 4, 2018; U.S. Pat. Nos. 8,241,573; 7,329,860 or 8,039,817; or US Pat. App. Pub. Nos. 2009/0272914 A1 published on Nov. 5, 2009 or 2012/0270305 A1 published on Oct. 25, 2012, each of which is incorporated herein by reference.

The compositions described herein can be packaged together as a kit for performing any of the methods disclosed herein. In some embodiments herein disclosed, the kits can contain one or more components of the rolling circle amplification mixture, the loading buffer, and the amplification buffer as disclosed above. For example, the kits can contain a loading buffer comprising a divalent metal cation and a branched polyelectrolyte in a low concentration described herein. The loading buffer can further comprise polymerases, buffers, reagents and substrate solutions for carrying out a rolling circle amplification reaction. The kits can also contain an amplification buffer comprising a divalent metal cation and a branched polyelectrolyte at a higher concentration described herein. The kits may contain additional reagents suitable for the detection, purification, and further processing of the amplified nucleic acids (e.g. concatemers) in downstream applications (e.g. sequencing). The kits can contain the compositions in separate containers. The kits can include one or more of appropriate packaging materials, containers for holding the components of the kit, and instructional materials for practicing the methods herein disclosed instructions.

EXAMPLES

Some aspects of the embodiments discussed above are disclosed in further detail in the following examples, which are not in any way intended to limit the scope of the present disclosure.

Example 1

A Non-limiting Example of RCA Reactions Using an Initiation Buffer Without a Replenishment Buffer This example demonstrates a set of non-limiting experiments of RCA amplification reactions carried out in a single initiation buffer (or a loading buffer) without a replenishment buffer (or an amplification buffer). In particular, this example demonstrates the effects of high concentrations of PAMAM on cluster intensities and spot counts.

Figure 3:
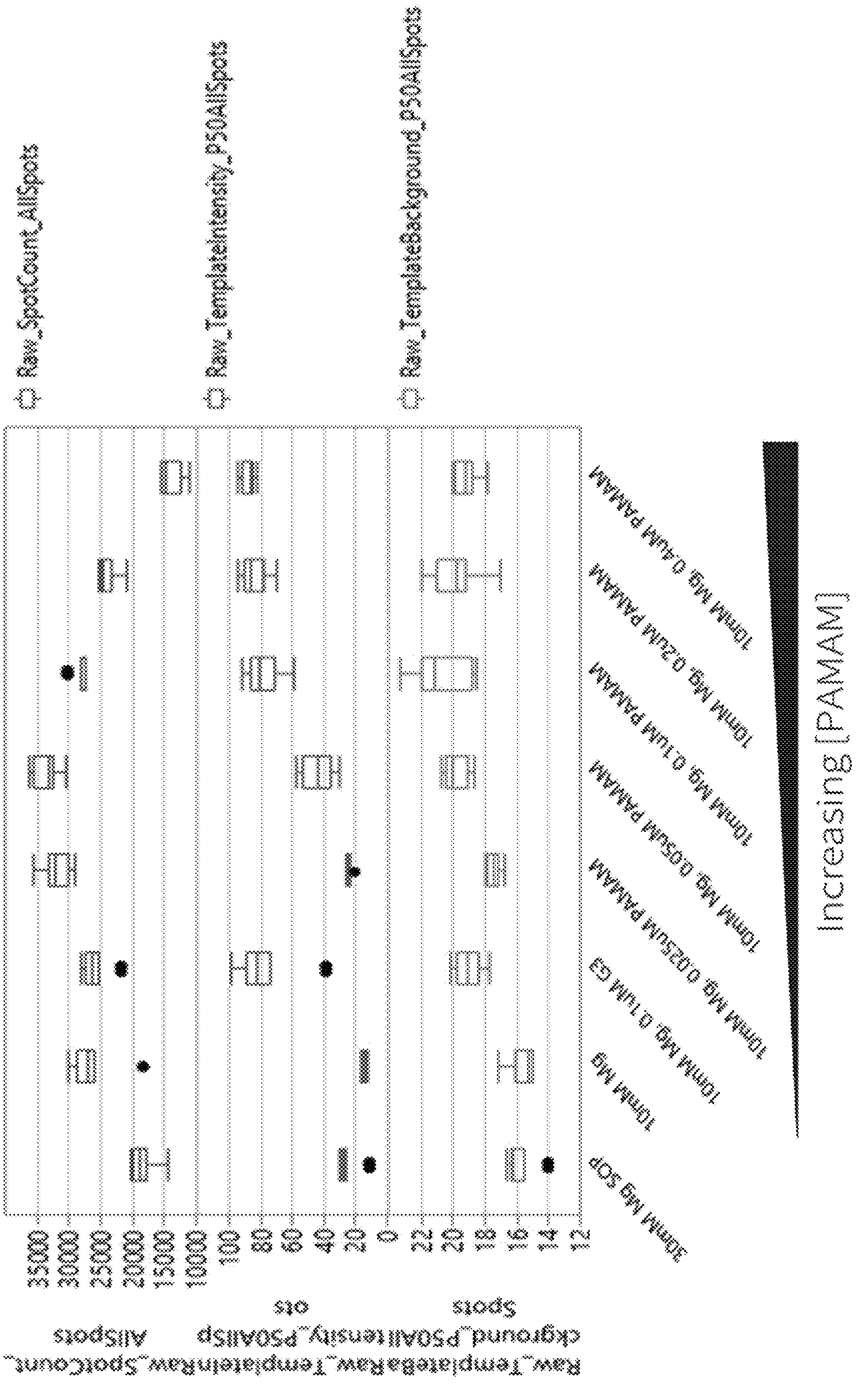
FIG. 3 is an exemplary graph showing background spot counts (lower panel), cluster intensity (middle panel) and all spot counts (upper panel) measured for RCA reactions with initiation mixes having the same $Mg^{2+}$ concentration (10 mM) and different PAMAM concentrations.

In this example, a RCA amplification is carried out in a single initiation buffer with no replenishment. FIG. 3 illustrates an exemplary plot showing background spot counts (lower panel), cluster intensity (middle panel) and all spot counts (upper panel) measured for RCA reactions with initiation mixes having a same $Mg^{2+}$ concentration (10 mM) and an increasing PAMAM concentration (from left to right on the lateral scale). The polymerase can be provided at 1000 U/ml and supplied in an enzyme storage buffer comprising e.g. 5% glycerol, 5 mM Tris-HCl pH 7.5, 0.01 mM EDTA, 0.1 mM DTT, 10 mM KCl, 0.05% NP-40, and 0.05% Tween®20.

The results show that increasing the concentration of PAMAM in a RCA reaction results in higher cluster intensity and a reduction in spot count. The benefits of using higher concentration of PAMAM to improve cluster intensity is hindered by the reduction in overall cluster produced.

Example 2

A Non-limiting Example of RCA Reactions Using an Initiation Buffer and a Replenishment Buffer With Different Compositions This example demonstrates sets of non-limiting experiments of RCA reactions carried out in an initiation buffer and a replenishment buffer with different compositions, such as different concentrations of metal ions (e.g. $Mg^{2+}$) and dendrimers (e.g. PAMAM) and with or without amplification enzymes (e.g. polymerase).

Figure 4:
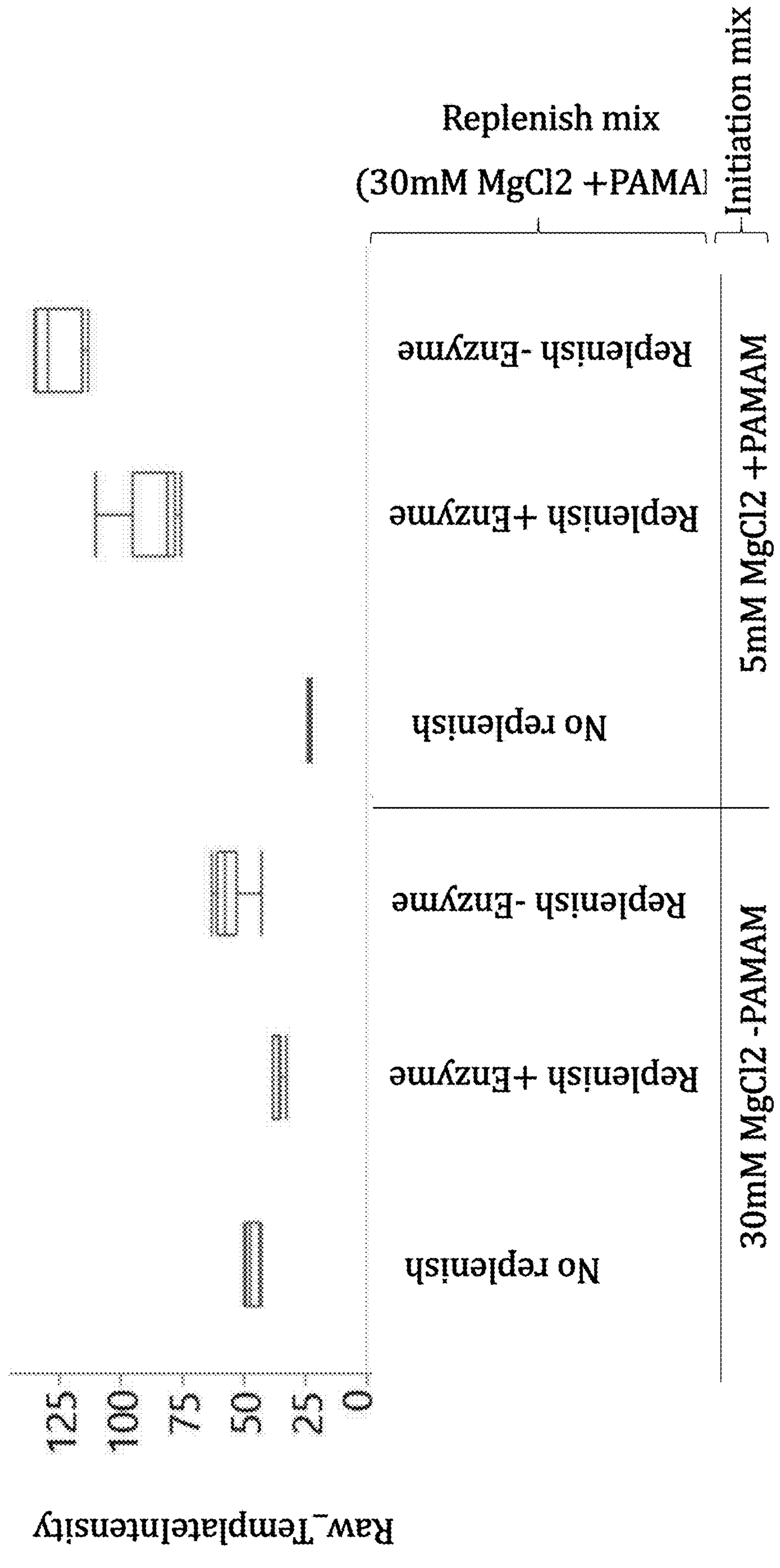
FIG. 4 is an exemplary graph showing cluster intensities measured for RCA reactions carried out in an initiation mix and a replenishment mix with different compositions.

FIG. 4 illustrates an exemplary plot showing cluster intensities measured for RCA reactions carried out in an initiation mix and a replenishment mix with different compositions.

In particular, as shown in FIG. 4, in one set of experiments, the initiation mix includes $MgCl_2$ in 30 mM without PAMAM (left three columns in FIG. 4). In another set of experiments, the initiation mix includes $MgCl_2$ in 5 mM with PAMAM (right three columns in FIG. 4). The replenishment mix used in all the experiments includes $MgCl_2$ in 30 mM with PAMAM except for the two control experiments which were carried out with no replenishment. The replenishment mix may or may not have the enzyme (i.e. polymerase).

The data shows that a higher concentration of $Mg^{2+}$ in the initiation mix is detrimental to the cluster intensity. The data also shows that replenishment with enzyme is less effective than replenishment without enzyme and also results in a significantly cost due to the use of enzyme. The results also suggest that increasing the $Mg^{2+}$ concentration in the replenishment mix can be beneficial to cluster intensity.

Figure 5:
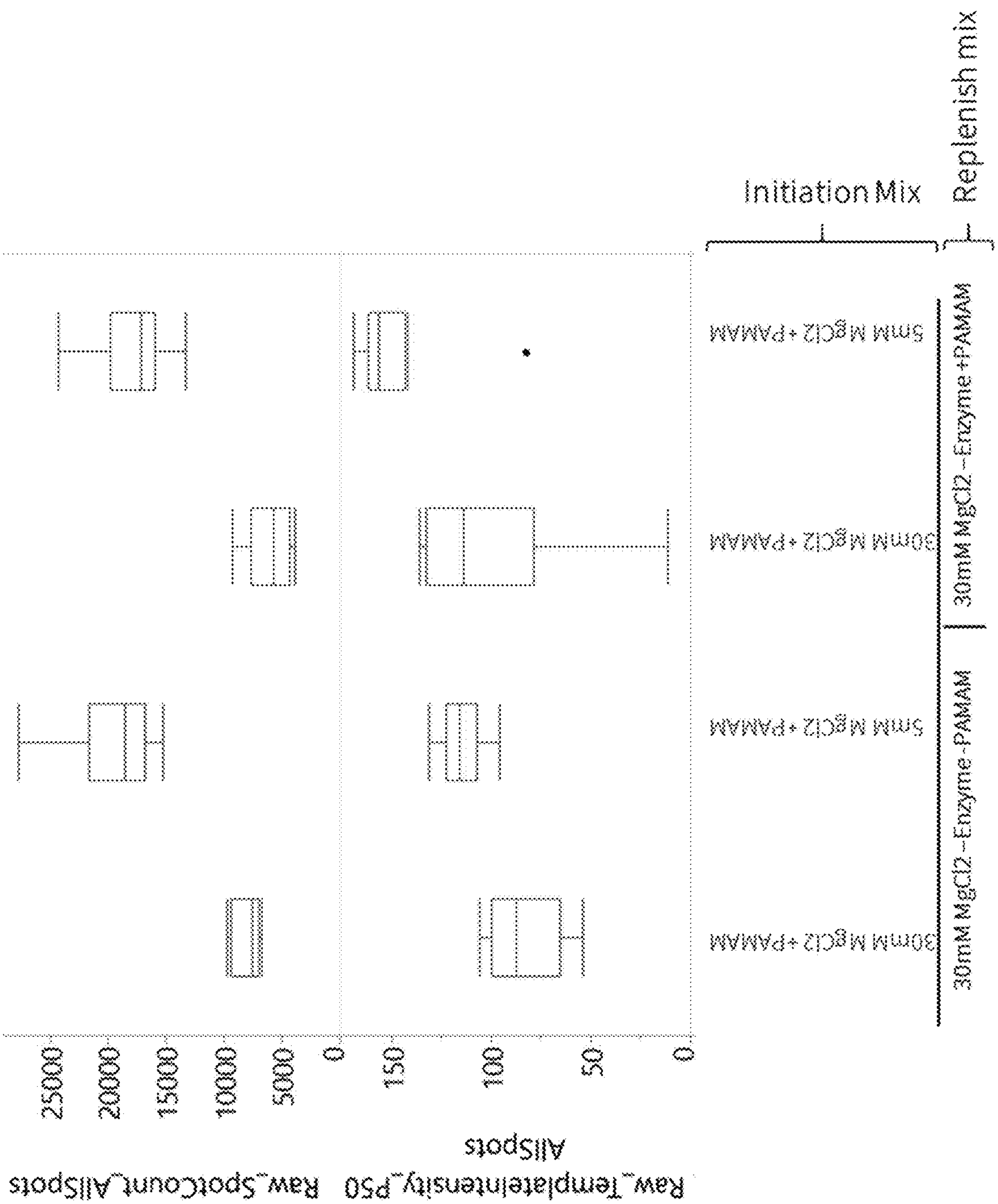
FIG. 5 is an exemplary graph showing cluster intensities (lower panels) and spot counts (upper panels) measured for RCA reactions carried out in an initiation mix and a replenishment mix with different compositions.

FIG. 5 illustrates an exemplary plot showing cluster intensities (lower panels) and spot counts (upper panels) measured for RCA reactions carried out with an initiation mix and a replenishment mix having different compositions.

In particular, as shown in FIG. 5, in one set of experiments, the replenishment mix includes $MgCl_2$ in 30 mM without PAMAM (left two columns in FIG. 5). In another set of experiments, the initiation mix includes $MgCl_2$ in 30 mM with PAMAM (right two columns in FIG. 5). In both sets of experiments, the replenishment mix does not contain enzymes. In each set of experiments, two different initiation mixes were tested: one initiation mix comprising $MgCl_2$ in 30 mM and the other initiation mix comprising $MgCl_2$ in 5 mM. Both initiation mixes contain PAMAM.

Comparison of the two different initiation buffers indicates that a high concentration $Mg^{2+}$ in the initiation buffer is significantly detrimental to spot counts. Comparison of the two different replenishment buffers indicates that a high concentration of $Mg^{2+}$ and PAMAM in the replenishment buffer is beneficial to cluster intensity.

Example 3

Measuring Polymerase Processivity in An Exemplary RCA Amplification Reaction This example demonstrates non-limiting experiments carried out to measure polymerase processivity in RCA reactions using an initiation mix and a replenishment mix with different compositions. In particular, this example demonstrates sets of exemplary experiments carried out to measure library copy numbers per nucleic acid cluster.

Procedures similar to the following steps were used to determine copy number per cluster: (1) Cluster RPCs with 3- and 8-hour amplification and hybridize cy3 probe: library input titration was performed, and copies per cluster should be same regardless of library input; (2) Elute cy3 probes with FMD; (3) Run samples on CE along with standard curve for each probe; (4) Use size standard to normalize peaks; (5) Use standard curve and elution volume to calculate number of eluted probes; (6) Rehybridize clusters/beads with cy5 probe; (7) Take images, analyze to get spot count per tile, and extrapolate median spot count to whole lane; and (8) Calculate number of probes per clusters.

Figure 6:
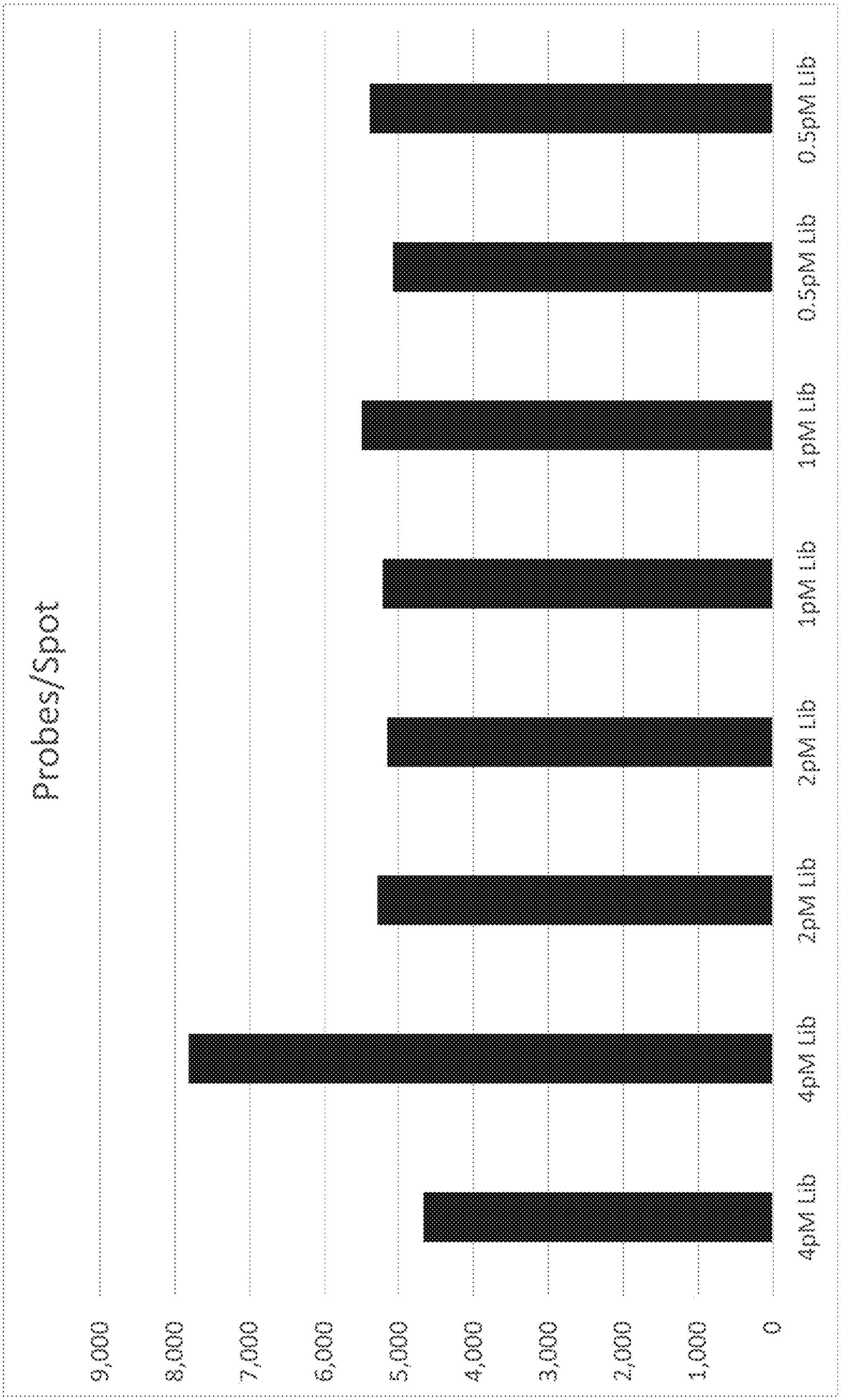
FIG. 6 is an exemplary graph showing the number of probes per cluster in a 3 hour rolling circle amplification reaction.
Figure 7:
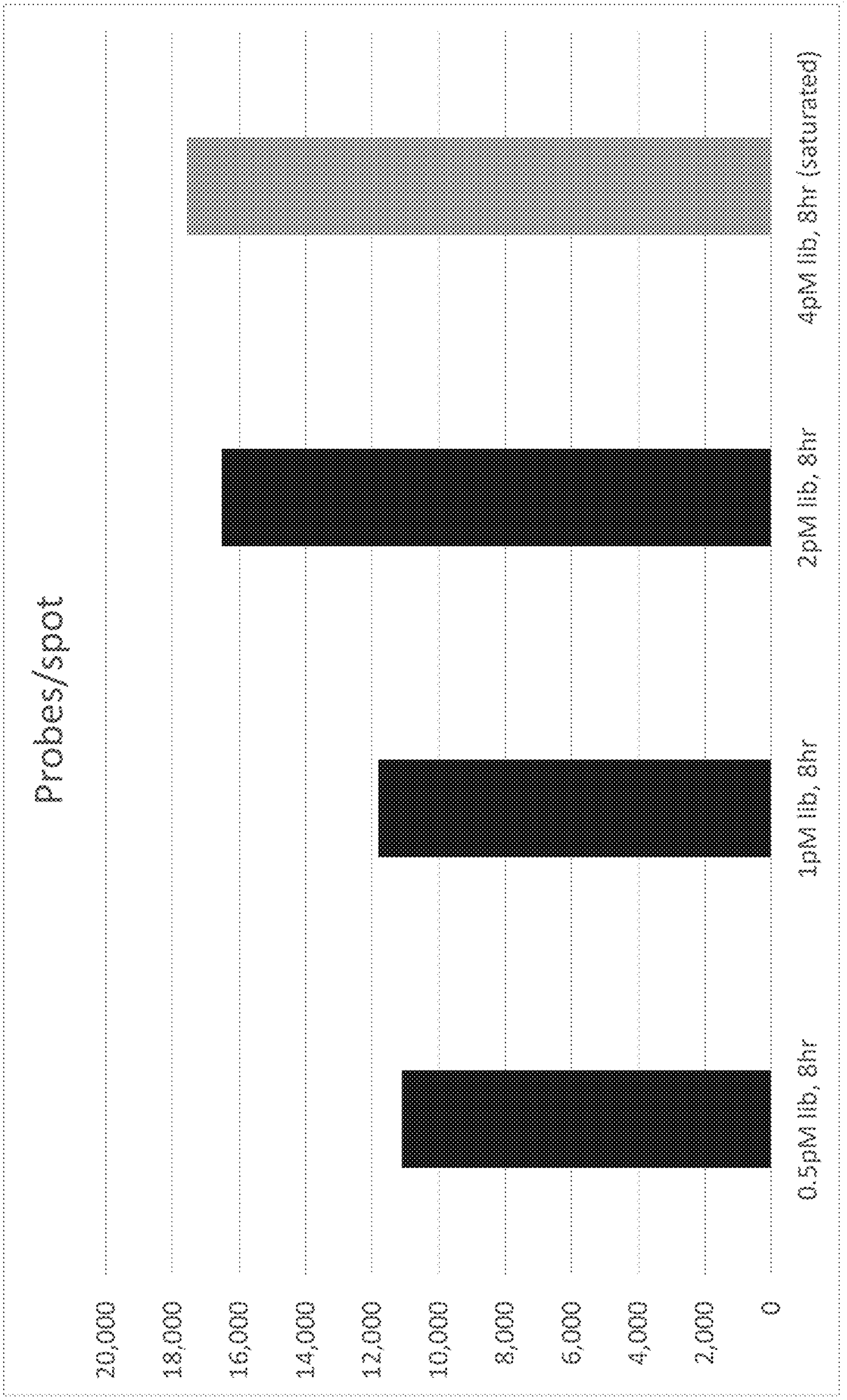
FIG. 7 is an exemplary graph showing the number of probes per cluster in a 8 hour rolling circle amplification reaction.

FIGS. 6-7 are two graphs showing results of amplification. FIG. 6 shows the number of probes per cluster with a 3 hour rolling circle amplification. The data indicates an average copy number of about 5 k per cluster after a 3-hour rolling circle amplification. FIG. 7 shows the number of probes per cluster with an 8-hour rolling circle amplification. The data indicates an average copy number of about 11 k-16 k per cluster after an 8-hour RCA amplification.

Given an average library size of 414 bases, a processivity of over 2M (2,070,000) bases cluster (based on measuring library copy number per cluster and average library size) can be achieved in a 3-hour rolling circle amplification and a processivity of over 4 M (4,554,000) to 6M (6,624,000) bases can be achieved in a 8-hour rolling circle amplification. The data shown in FIGS. 6-7 demonstrate the continued activity of the single polymerase amplification of each spot subsequent to addition of replenishment buffer.

It is understood that polymerase extension through RCA is provided as an example of an enzymatic reaction benefitting from reagent replenishment. However, the disclosure herein is applicable to a broad range of enzymatic reactions where reagent exhaustion limits the formation of a reaction product. In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., " a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of rolling circle amplification (RCA) for nucleic acids, comprising (a) contacting a circular DNA template and a capture primer with a RCA mixture in a vessel for a first duration to form amplified concatemers of the DNA template, wherein the RCA mixture comprises a DNA polymerase, a dNTP mix, a loading buffer comprising a divalent metal cation and a branched polyelectrolyte species, and (b) replacing the RCA mixture in the vessel with an amplification buffer after the first duration to form amplified concatemers of the DNA template, wherein the amplification buffer does not comprise any DNA polymerase and comprises the divalent metal cation and the branched polyelectrolyte species, wherein the branched polyelectrolyte species in the amplification buffer is in a concentration at least about 2-fold higher than in the loading buffer, and wherein the branched polyelectrolyte species is a polycationic dendrimer.

2. The method of claim 1, wherein the vessel is a flow cell.

3. The method of claim 1, wherein the DNA template is a single-stranded DNA.

4. The method of claim 1, wherein the divalent metal cation is a magnesium cation.

5. The method of claim 1, wherein the polycationic dendrimer is a poly(amidoamine) (PAMAM) dendrimer.

6. The method of claim 5, wherein the PAMAM dendrimer is a G3 PAMAM.

7. The method of claim 1, wherein the first duration is about 10 minutes to about 60 minutes.

8. The method of claim 1, wherein the formation of amplified concatemers of the DNA template in step (b) is faster than the formation of amplified concatemers of the DNA template in step (a).

9. The method of claim 1, further comprising sequentially introducing one or more additional amplification buffers to the vessel at least once after step (b), wherein the additional amplification buffers do not comprise any DNA polymerase and comprise the divalent metal cation and the branched polyelectrolyte species.

10. The method of claim 9, wherein the amplification buffer is different in composition from at least one of the additional amplification buffers.

11. The method of claim 1, wherein the divalent metal cation in the amplification buffer is in a concentration of at least 10 mM.

12. The method of claim 1, wherein the divalent metal cation in the amplification buffer is in a concentration at least about 2-fold higher than in the loading buffer.

13. The method of claim 1, wherein the divalent metal cation in the loading buffer is in a concentration from about 0.001 mM to about 10 mM.

14. The method of claim 1, wherein the branched polyelectrolyte in the amplification buffer is in a concentration of at least 5 μM.

15. The method of claim 1, wherein the branched polyelectrolyte in the loading buffer is in a concentration from about 0.001 μM to about 1 μM.

16. The method of claim 1, wherein contacting the circular DNA template and the capture primer with the RCA mixture comprises formation of polymerase-nucleic acid complexes, and after introducing the amplification buffer into the vessel, at least about 50% of the DNA polymerase bound to the polymerase-nucleic acid complexes are retained.

17. The method of claim 16, wherein introducing the amplification buffer into the vessel removes DNA polymerase that is not in the polymerase- nucleic acid complexes from the vessel.

18. The method of claim 1, wherein the branched polyelectrolyte species in the loading buffer is in a concentration from about 0.001 μM to about 1 μM and the branched polyelectrolyte species in the amplification buffer is in a concentration of at least 5 μM.

* * * * *